(12) United States Patent
Tang et al.

(10) Patent No.: US 12,616,804 B2
(45) Date of Patent: May 5, 2026

(54) NEBULIZER

(71) Applicant: MICROBASE TECHNOLOGY CORP., Taoyuan City (TW)

(72) Inventors: Chi-Jui Tang, Taoyuan City (TW); Jo-Ling Wu, Taoyuan City (TW)

(73) Assignee: MICROBASE TECHNOLOGY CORP., Taoyuan City (TW)

( * ) Notice: Subject to any disclaimer, the term of this patent is extended or adjusted under 35 U.S.C. 154(b) by 754 days.

(21) Appl. No.: 18/013,903

(22) PCT Filed: Jun. 28, 2021

(86) PCT No.: PCT/CN2021/102677
§ 371 (c)(1),
(2) Date: Dec. 30, 2022

(87) PCT Pub. No.: WO2022/001932
PCT Pub. Date: Jan. 6, 2022

(65) Prior Publication Data
US 2023/0321365 A1     Oct. 12, 2023

Related U.S. Application Data

(60) Provisional application No. 63/045,841, filed on Jun. 30, 2020.

(51) Int. Cl.
*A61M 15/00*      (2006.01)
*A61M 11/00*      (2006.01)
*B05B 11/10*      (2023.01)

(52) U.S. Cl.
CPC ...... *A61M 15/0081* (2014.02); *A61M 11/007* (2014.02); *A61M 15/0073* (2014.02); *B05B 11/108* (2023.01); *B05B 11/1091* (2023.01)

(58) Field of Classification Search
CPC .......... A61M 15/0081; A61M 15/0041; A61M 15/0068; A61M 15/0065; A61M 15/007; A61M 11/006; B05B 11/108
See application file for complete search history.

(56) References Cited

U.S. PATENT DOCUMENTS 6,234,366 B1     5/2001   Fuchs
10,576,222 B2    3/2020   Eicher et al.
(Continued)

FOREIGN PATENT DOCUMENTS

CN          1360523 A      7/2002
CN          102171111 A     8/2011
(Continued)

OTHER PUBLICATIONS

Search Report issued on Aug. 23, 2024 for EP application No. 21832545.4.
(Continued)

*Primary Examiner* — Brandy S Lee
*Assistant Examiner* — Sara K Toich
(74) *Attorney, Agent, or Firm* — Li & Cai Intellectual Property Office

(57)     ABSTRACT

A nebulizer and a storage device are provided. The nebulizer includes a casing, an atomization module fixed to the casing, a rotating module rotatably assembled to the casing, a linking module assembled to the rotating module, and a locking module. The linking module is configured to be connected to a bottom of the container bottle, and the starting module is configured to drive the nebulizer by being pushed, thereby enabling liquid in the container bottle to be atomized toward an outside of the nebulizer through the atomization module in an atomization process. The locking module is configured to be connected to a bottom of the container bottle. When the nebulizer completes a predeter-
(Continued)

mined number of times of the atomization process, the locking mechanism is moved toward the casing and is then limited to restrict an operation of the nebulizer. Accordingly, after the nebulizer completes the predetermined number of times of the atomization process, the locking module can restrict rotation of the rotating module for preventing the nebulizer from using the container bottle arranged therein.

7 Claims, 34 Drawing Sheets

(56)                    References Cited

U.S. PATENT DOCUMENTS

| | | | |
|---|---|---|---|
| 2002/0047021 A1* | 4/2002 | Blacker | G06M 1/041 |
| | | | 222/23 |
| 2005/0194006 A1* | 9/2005 | Hoang | A61M 15/009 |
| | | | 128/200.14 |
| 2007/0062518 A1* | 3/2007 | Geser | A61M 15/0081 |
| | | | 128/200.14 |
| 2009/0211576 A1* | 8/2009 | Lehtonen | A61M 15/0081 |
| | | | 128/203.12 |
| 2013/0125880 A1 | 5/2013 | Holakovsky et al. | |
| 2014/0263456 A1 | 9/2014 | Barber et al. | |
| 2015/0040890 A1* | 2/2015 | Besseler | A61M 15/0038 |
| | | | 128/200.14 |
| 2016/0207669 A1 | 7/2016 | Li et al. | |
| 2017/0072147 A1* | 3/2017 | Eicher | A61M 11/007 |
| 2020/0179620 A1 | 6/2020 | Wuttke et al. | |
| 2021/0322685 A1* | 10/2021 | Lin | A61M 31/00 |
| 2022/0047823 A1* | 2/2022 | Säll | B05B 11/1091 |

FOREIGN PATENT DOCUMENTS

| | | | | |
|---|---|---|---|---|
| CN | 204587620 U | 8/2015 | | |
| CN | 204606793 U | 9/2015 | | |
| CN | 106232165 A | 12/2016 | | |
| CN | 106232166 A | 12/2016 | | |
| CN | 107961433 A | 4/2018 | | |
| CN | 110269476 A | 9/2019 | | |
| CN | 110433361 A | 11/2019 | | |
| CN | 215515024 U | 1/2022 | | |
| EP | 2044967 A1 | 4/2009 | | |
| JP | 2006256652 A | 9/2006 | | |
| JP | 2010274232 A | 12/2010 | | |
| WO | WO-9724586 A1 * | 7/1997 | G01F 15/06 | |
| WO | WO-2006130100 A1 * | 12/2006 | A61M 15/0073 | |
| WO | WO2018036388 A1 | 3/2018 | | |

OTHER PUBLICATIONS

International Search Report issued on Oct. 9, 2021 for PCT application No. PCT/CN2021/102677.

* cited by examiner

NEBULIZER

FIELD OF THE DISCLOSURE

The present disclosure relates to a nebulizer, and more particularly to a nebulizer and a storage device each having a limiting operation count.

BACKGROUND OF THE DISCLOSURE

A conventional nebulizer can have an internal space provided for assembling and receiving a replaceable container therein, allowing the conventional nebulizer to implement an atomization process to a liquid in the replaceable container through a structural design thereof. However, the conventional nebulizer does not have an accurate mechanism for limiting a usage count thereof, so that the conventional nebulizer may be operated unknowingly by a user for an unreasonable number of times.

SUMMARY OF THE DISCLOSURE

In response to the above-referenced technical inadequacies, the present disclosure provides a nebulizer and a storage device to effectively improve on the issues associated with conventional nebulizers.

In one aspect, the present disclosure provides a nebulizer, which includes: a casing defining a rotation axis; an atomization module fixed in the casing and located at the rotation axis; a starting module assembled to the casing; a rotating module including: a rotating mechanism inserted into the casing and rotatably assembled to the casing along the rotation axis; and a cover assembled to the rotating mechanism, wherein the cover and the casing jointly define an interior space; a pusher assembled to an inner bottom of the cover; a linking module assembled to the rotating module and configured to provide for a container bottle to be disposed therein, wherein the rotating module is rotatable by a predetermined angle to move the linking module, so that the linking module is moved from an initial position to a standby position along the rotation axis by pressing against the casing, and the linking module at the standby position is retained by the starting module; wherein, when the linking module is at the standby position, the starting module is configured to drive the linking module to be moved to the initial position by being pushed, thereby enabling liquid in the container bottle to be atomized toward an outside of the nebulizer through the atomization module in an atomization process; and a locking module configured to be connected to a bottom of the container bottle, wherein the locking module includes: a trigger mechanism corresponding in position to the pusher; and a locking mechanism assembled to the rotating mechanism, wherein each time the atomization process is completed by the nebulizer, the locking module moves back and forth along the rotation axis once, so that the trigger mechanism is moved toward the locking mechanism through being pressed by the pusher; wherein, when the nebulizer completes a predetermined number of times of the atomization process, the trigger mechanism pushes the locking mechanism, so that the locking mechanism is moved toward the casing and is then limited in position to restrict a rotation of the rotating mechanism.

Preferably, the trigger mechanism includes: a rotation member; and a progressing member connected to the rotation member, wherein the rotation member is rotatable to drive the progressing member to be moved; wherein, when the nebulizer completes the predetermined number of times of the atomization process, the progressing member is driven by the rotation member until the locking mechanism is moved by the progressing member, so that the locking mechanism is moved to the casing and limited in position.

Preferably, the locking module includes a box body configured to be connected to the bottom of the container bottle, wherein the box body has an opening arranged on a movement path of the locking mechanism, and the trigger mechanism is assembled in the box body, and wherein, when the nebulizer completes the predetermined number of times of the atomization process, the progressing member is driven by the rotation member until the opening is closed off by the progressing member and the locking mechanism is pushed by the progressing member.

Preferably, the casing has a locking slot, and the locking mechanism includes: an elastic member disposed in the locking slot; and a locking rod having a rod body and a protruding portion that extends from the rod body, wherein the rod body corresponds in position to the opening, and the protruding portion corresponds in position to the locking slot; wherein, when the nebulizer completes the predetermined number of times of the atomization process, the rod body is moved by the progressing member, so that the protruding portion moves into the locking slot and presses the elastic member.

Preferably, the locking module includes a box body configured to be connected to the bottom of the container bottle, the trigger mechanism is assembled to the box body and includes a driving member, and the rotation member includes: a screw rod pivotally connected to the box body, wherein the progressing member is slidably disposed on the box body and is threadedly engaged with the screw rod; and a plurality of teeth disposed on the screw rod, wherein each time the atomization process is completed by the nebulizer, the driving member is configured to be pressed and moved by the pusher in a manner that rotates the screw rod by driving at least one of the teeth to move, such that the progressing member is then driven to be moved.

Preferably, the driving member includes: a plate-like body; a spring abutting against the box body and the plate-like body, wherein the spring tends to push the plate-like body toward a bottom of the box body; and a hook formed on the plate-like body and corresponding in position to at least one of the teeth; wherein, each time the atomization process is completed by the nebulizer, the plate-like body moves in the box body back and forth once through the pusher and the spring, so that the hook rotates the screw rod by moving at least one of the teeth.

Preferably, the locking module includes a box body configured to be connected to the bottom of the container bottle, the trigger mechanism is assembled in the box body, and the rotation member includes a turntable corresponding in position to the pusher and a stud that is erectly formed on the turntable, and wherein the progressing member includes: a progressing plate threadedly engaged with the stud, wherein the turntable is rotatable through being pressed by the pusher so as to drive the progressing plate to be moved along the stud; and a progressing rod slidably disposed on a top of the box body and being separate from the progressing plate; wherein, when the nebulizer completes the predetermined number of times of the atomization process, the progressing plate is driven by the rotation member until the progressing rod is moved by the progressing plate, so that the progressing rod pushes the locking mechanism to be moved toward the casing and to be limited in position.

Preferably, the box body has a limiting structure formed on an inner lateral wall thereof and having a first height with respect to a bottom of the box body, wherein the first height is lower than a second height of the stud with respect to the bottom of the box body, wherein, when the progressing plate is located at a position lower than the first height, the progressing plate driven by the turntable is unable to be rotated through being limited by the limiting structure, and is only movable along the stud in a straight line, and wherein, when the progressing plate is located at a position higher than the first height, the progressing plate is configured to be driven by the turntable, so that the progressing plate and the turntable jointly rotate to push the progressing rod.

In another aspect, the present disclosure provides a storage device, which includes: a container bottle; and a locking module including: a box body connected to a bottom of the container bottle and having an opening; and a trigger mechanism assembled in the box body and including: a rotation member; and a progressing member connected to the rotation member, wherein the rotation member is rotatable to drive the progressing member to be moved toward the opening; wherein, when the rotation member is rotated for a predetermined number of times, the progressing member is driven by the rotation member until the opening is closed off by the progressing member.

Preferably, the box body is fixed to the bottom of the container bottle in an undetachable manner.

Therefore, the locking module of the nebulizer provided by the present disclosure is in cooperation with the casing and the rotating module through structural design thereof, so that after the nebulizer completes the predetermined number of times of the atomization process, the locking module can restrict the rotation of the rotating module for preventing the nebulizer from using the container bottle assembled therein.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
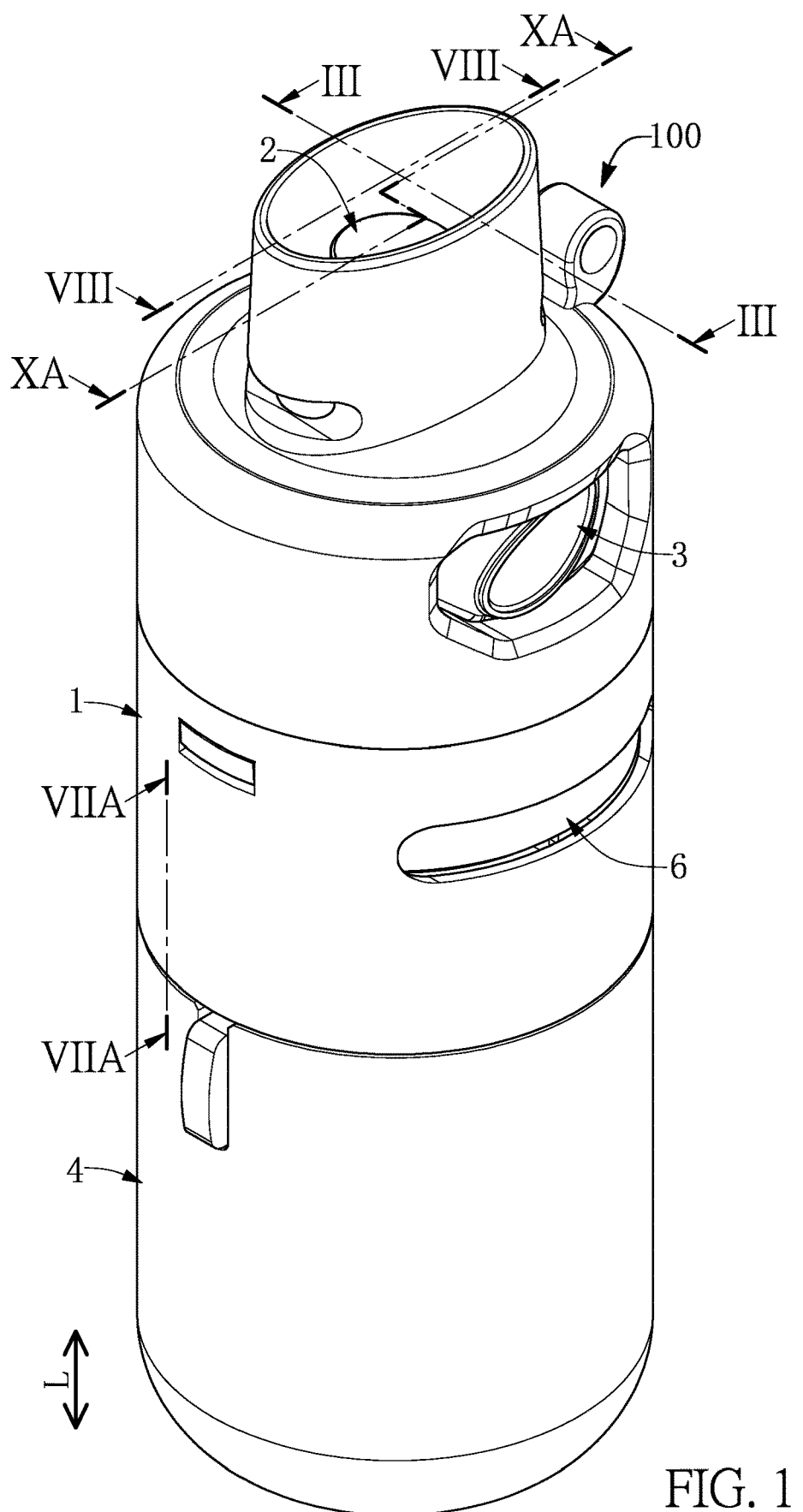
FIG. 1 is a perspective view of a nebulizer according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
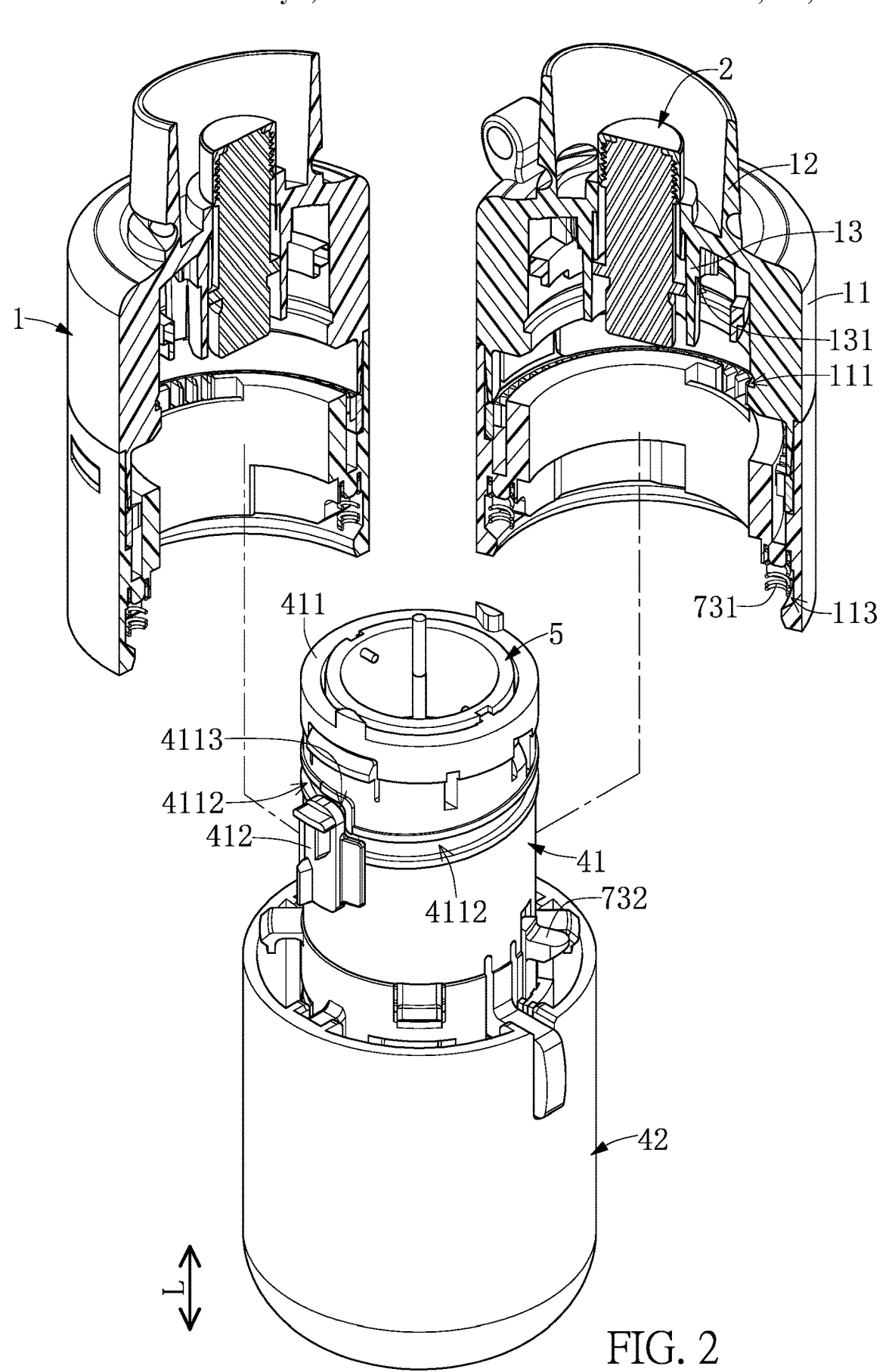
FIG. 2 is an exploded view of the nebulizer according to the first embodiment of the present disclosure.
Figure 3:
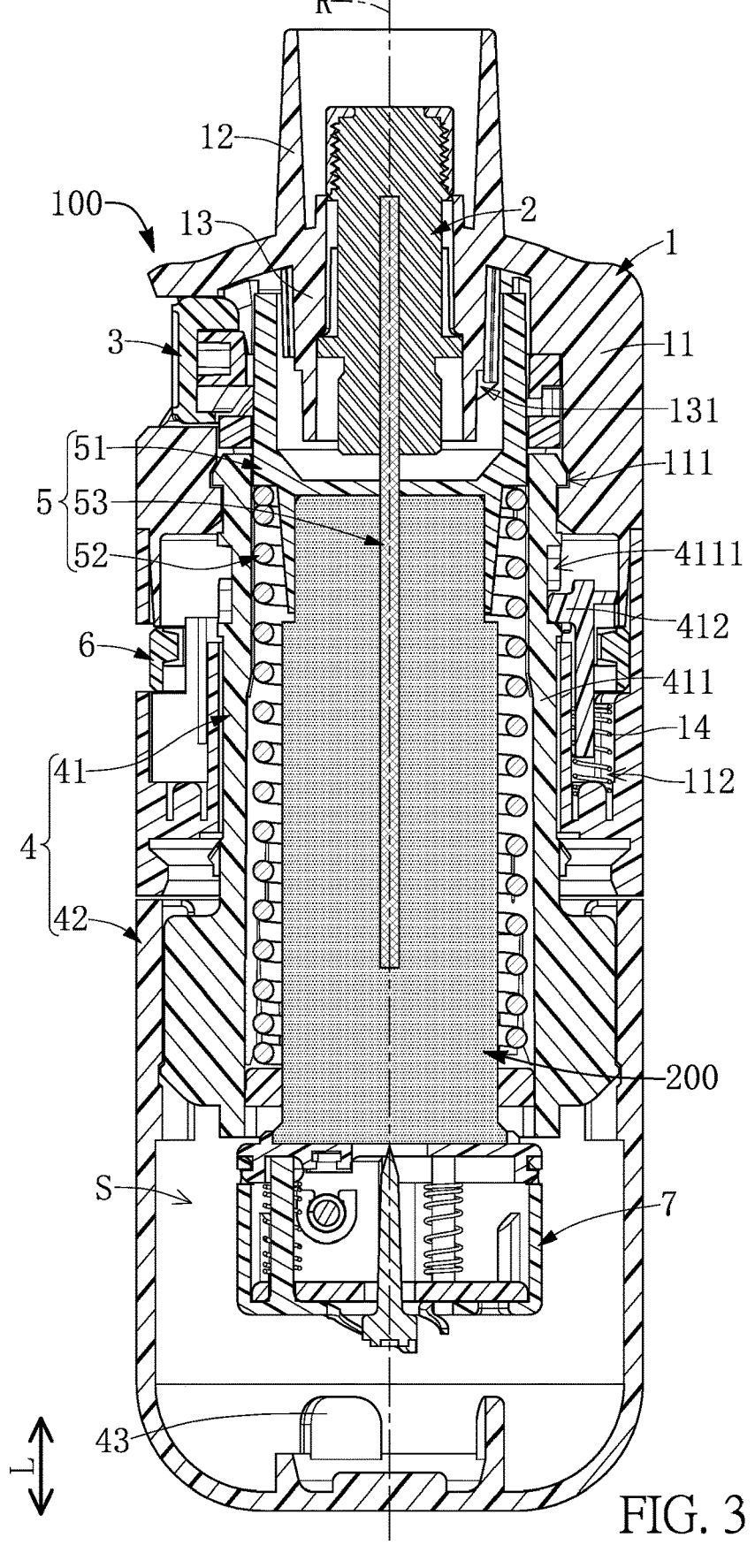
FIG. 3 is a cross-sectional view taken along line III-III of FIG. 1.

Referring to FIG. 1 to FIG. 10C, a first embodiment of the present disclosure provides a nebulizer 100 (or a sprayer 100). As shown in FIG. 1 to FIG. 3, the nebulizer 100 is preferably limited to be driven for spraying through mechanical structure, not electricity. The nebulizer 100 is configured to provide a container bottle 200 (e.g., a medicine bottle) to be disposed therein, and the nebulizer 100 can atomize liquid (e.g., a medicine liquid) in the container bottle 200 for a user.

In the present embodiment, the nebulizer 100 includes a casing 1, an atomization module 2 fixed in the casing 1, a starting module 3 (manipulatably) assembled to the casing 1, a rotating module 4 rotatably assembled to the casing 1, a linking module 5 assembled to the rotating module 4, a counter 6 movably disposed between the casing 1 and the rotating module 4, and a locking module 7 that is configured to be connected to a bottom of the container bottle 200. The locking module 7 and the container bottle 200 in the present embodiment can be jointly defined as a storage device that can be independently used (e.g., sold) or can be used in cooperation with other components.

It should be noted that the nebulizer 100 in the present embodiment is described in cooperation with the above components, but the present disclosure is not limited thereto. For example, in other embodiments of the present disclosure not shown in the drawings, the nebulizer 100 can be provided without at least one of the counter 6 and the locking module 7 according to design requirements. The following description describes the basic configuration of the nebulizer 100, and then describes a counting function and a locking function of the nebulizer 100.

Basic Configuration of Nebulizer According to the First Embodiment

The nebulizer 100 described in the present embodiment takes the casing 1 to be regarded as a fixing (or unmovable) component for explaining connection between other components, but the present disclosure is not limited thereto. Moreover, the casing 1 in the present embodiment is a substantially tubular structure that is formed by assembling multiple parts. The casing 1 defines a rotation axis R substantially overlapped with a center axis of the casing 1, but the present disclosure is not limited thereto.

Figure 4:
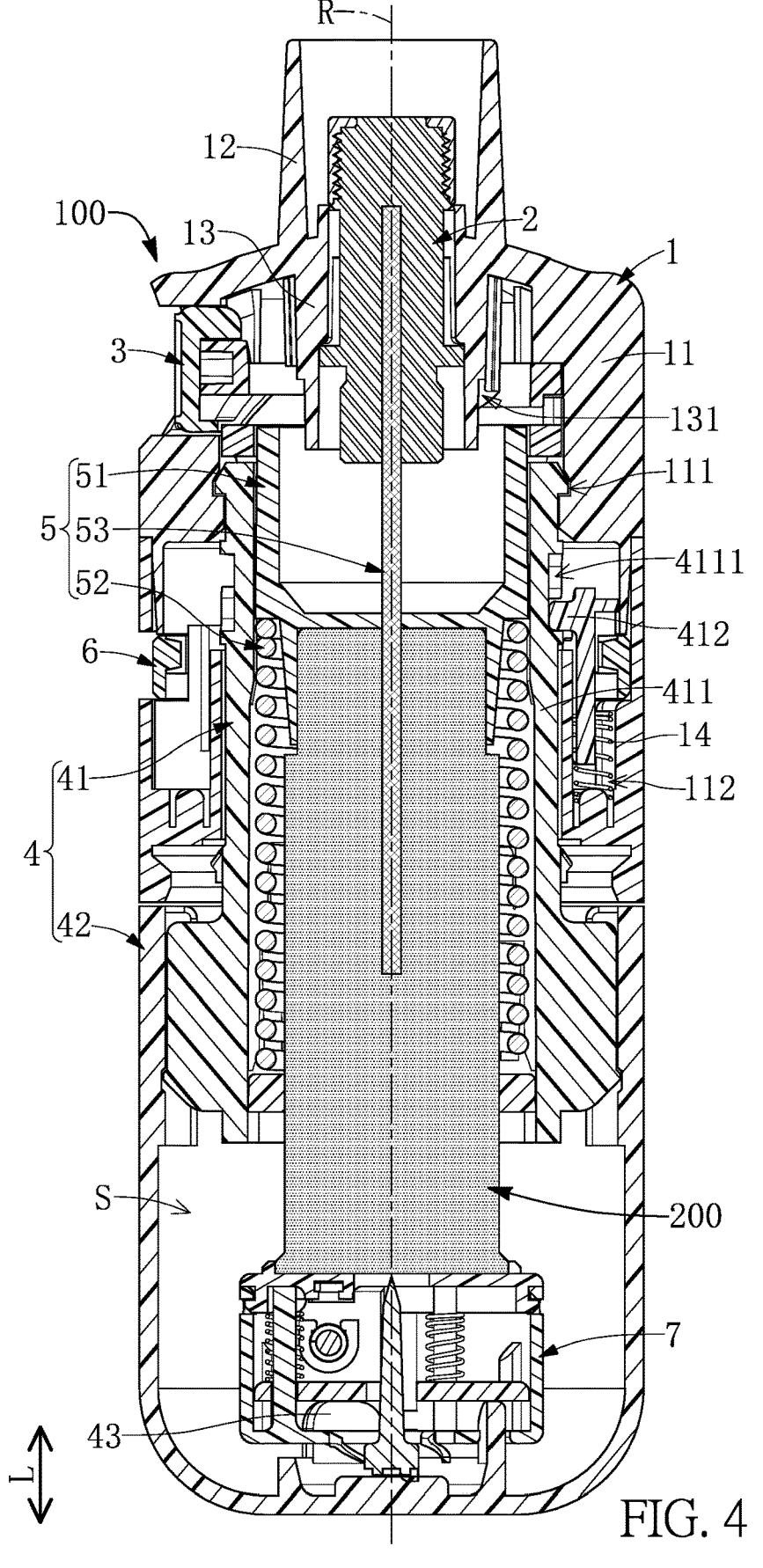
FIG. 4 is a cross-sectional view showing the nebulizer of FIG. 3 at a standby position.

Specifically, as shown in FIG. 2 to FIG. 4, the casing 1 in the present embodiment includes a housing segment 11, a spraying segment 12 connected to a top end of the housing segment 11, and an operation segment 13 that is arranged between the housing segment 11 and the spraying segment 12. The starting module 3 is engaged in the housing segment 11 and is partially exposed from the housing segment 11 for providing a manipulation to the user. The housing segment 11 has an annular slot 111 that is recessed in an inner side of the housing segment 11 and that has a center of circle located at the rotation axis R.

The operation segment 13 is formed to fix the atomization module 2 so as to arrange the atomization module 2 to be located at the rotation axis R. The spraying segment 12 is substantially in a tubular shape and surrounding a top of the atomization module 2, and the spraying segment 12 is configured to guide liquid that is atomized by the atomization module 2. The operation segment 13 in the present embodiment has a spiral guiding surface 131 that is arranged on an outer side of the operation segment 13 and that surrounds the rotation axis R.

The rotating module 4 in the present embodiment includes a rotating mechanism 41 inserted into the casing 1 and a cover 42 that is assembled to the rotating mechanism 41. The rotating mechanism 41 is rotatably assembled to the casing 1 along the rotation axis R (e.g., the rotating mechanism 41 is rotatably engaged in the annular slot 111 of the housing segment 11), and the cover 42 and the casing 1 jointly define an interior space S.

Figure 5:
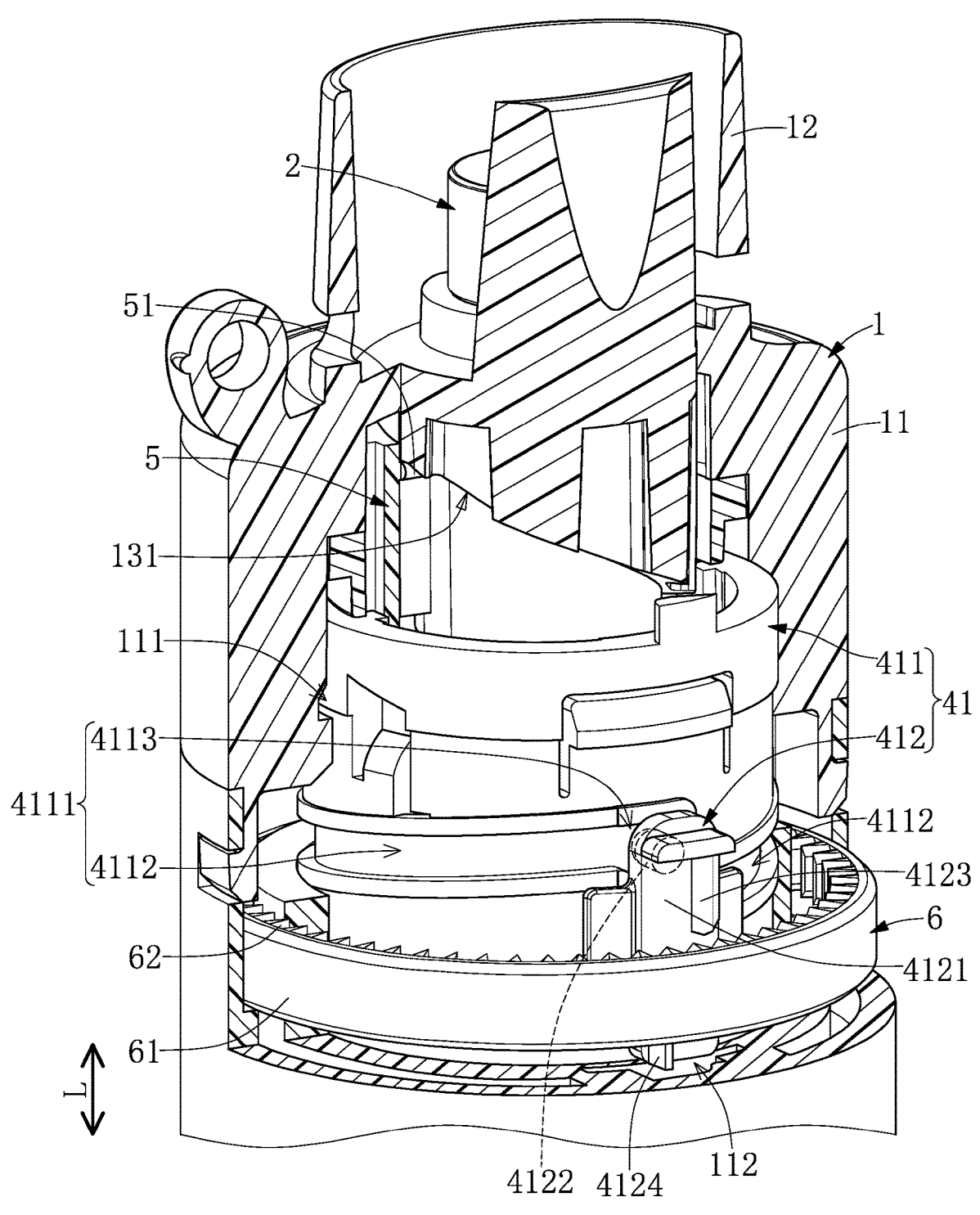
FIG. 5 is a perspective cross-sectional view showing a part of the nebulizer according to the first embodiment of the present disclosure.
Figure 6:
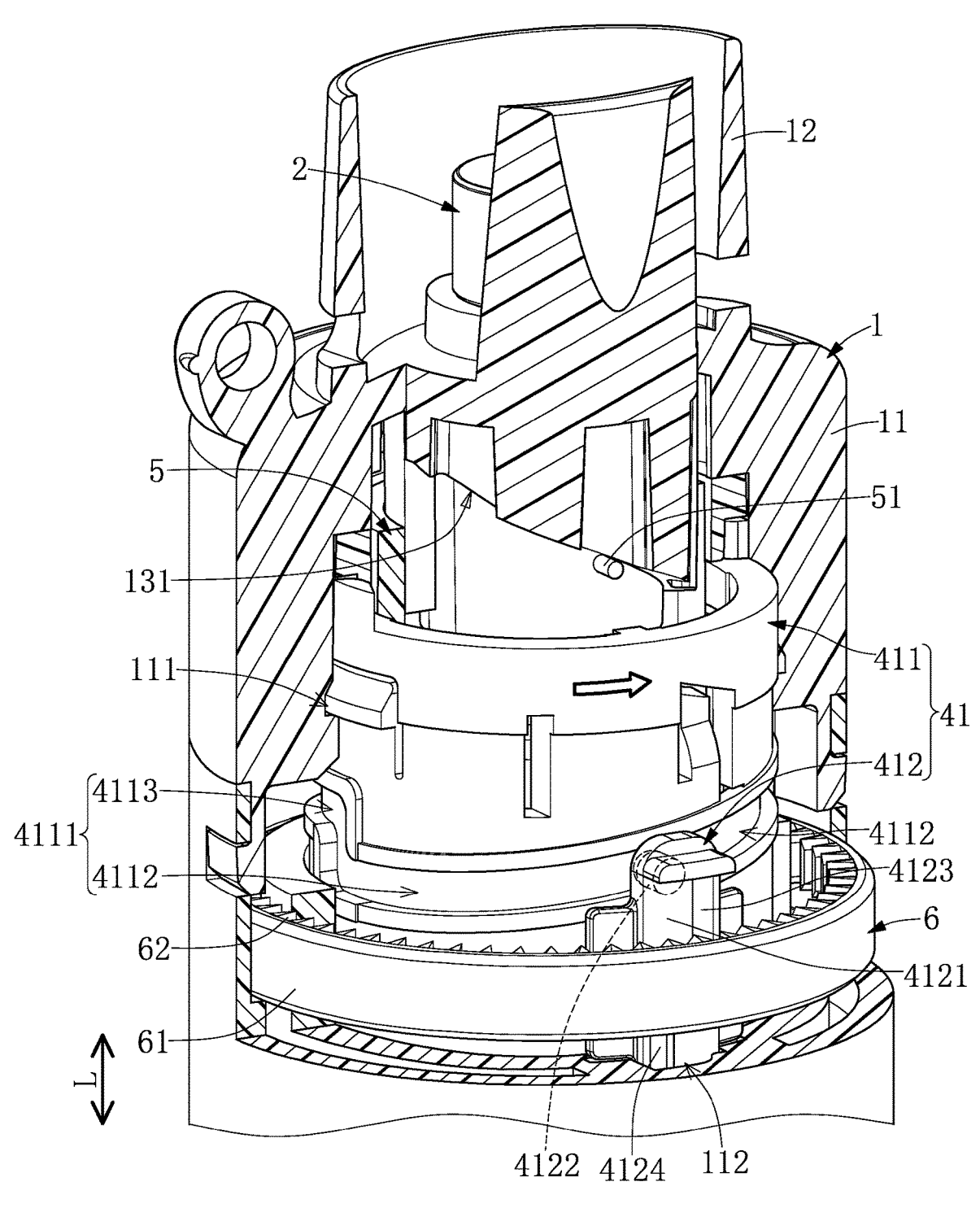
FIG. 6 is a schematic view showing a movement of the nebulizer after that of FIG. 5.

The linking module 5 is configured to provide for the container bottle 200 to be disposed therein, and includes a linking member 51 and a percussion spring 52. One end portion of the linking member 51 is abutted against the spiral guiding surface 131 of the casing 1 (as shown in FIG. 5 and FIG. 6), and another end portion of the linking member 51 is configured to hold a top end of the container bottle 200. The linking member 51 has a transmission pipe 53 inserted into the atomization module 2 and the container bottle 200, so that the container bottle 200 can be in spatial communication with the atomization module 2.

Moreover, the linking member 51 is limited (or linked) to the rotating mechanism 41 and is slidably disposed on the rotating mechanism 41 along a straight direction L parallel to the rotation axis R (e.g., the linking member 51 and the rotating mechanism 41 are simultaneously rotatable, and the linking member 51 is also movable along the straight direction L relative to the rotating mechanism 41), and the percussion spring 52 surrounds the container bottle 200.

In summary, the rotating module 4 is rotatable by a predetermined angle (relative to the casing 1) to move the linking module 5, so that the linking module 5 is moved from an initial position to a standby position (e.g., as shown in FIG. 3 to FIG. 6, the linking member 51 is pressed and is moved along the spiral guiding surface 131 so as to deform the percussion spring 52 for storing an elastic force) along the rotation axis R by pressing against the casing 1, and the linking module 5 at the standby position is retained by the starting module 3.

When the linking module 5 is at the standby position (as shown in FIG. 4), the starting module 3 is configured to drive the linking module 5 to be moved to the initial position by being pushed (e.g., the starting module 3 can release the elastic force of the percussion spring 52 by being pushed), thereby enabling liquid in the container bottle 200 to be atomized toward an outside of the nebulizer 100 through the atomization module 2 in an atomization process.

In addition, the limiting and driving relationship between the starting module 3 and the linking module 5 is a common technical means in the field and can be adjusted or changed according to design requirements, so that the present embodiment will be omitted herein for the sake of brevity.

Counting Function of Nebulizer According to the First Embodiment

The above description describes the basic configuration of the nebulizer 100 of the present embodiment, and the following description describes a counting function of the nebulizer 100 of the present embodiment. As shown in FIG. 5 to FIG. 7C, when the rotating module 4 is rotated by the predetermined angle, the rotating module 4 can drive the counter 6 to be rotated by a counting angle, and a specific structure of the nebulizer 100 for the counting function can be adjusted or changed according to design requirements, so that the following description of the present embodiment only describes one of possible structures of the nebulizer 100, but the present disclosure is not limited thereto.

Specifically, as shown in FIG. 3 to FIG. 6, the casing 1 has a limiting slot 112 formed in an interior thereof (e.g., an inner side of the bottom of the housing segment 11), and the casing 1 further includes a returning elastic member 14 disposed in the limiting slot 112. The returning elastic member 14 in the present embodiment is a spring that can be elastically compressed along the straight direction L.

The rotating mechanism 41 includes a tube 411 and a driving block 412. One end of the tube 411 (e.g., a top end of the tube 411 shown in FIG. 3) is engaged in the annular slot 111 of the housing segment 11, and another end of the tube 411 (e.g., a bottom end of the tube 411 shown in FIG. 3) is assembled to the cover 42. The tube 411 has a rail slot 4111 (receded in an outer surface thereof), and the driving block 412 is disposed in the limiting slot 112 and is movably assembled to the rail slot 4111.

Figure 7A:
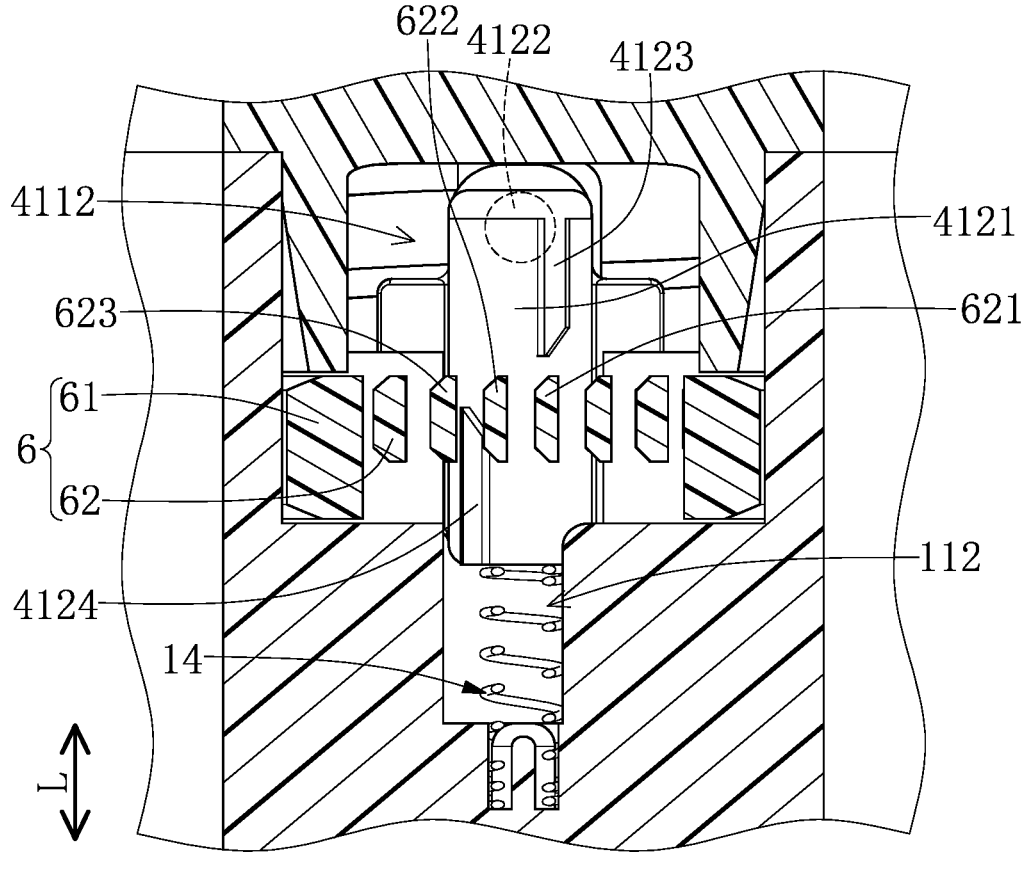
FIG. 7A is a cross-sectional view taken along line VIIA-VIIA of FIG. 1.
Figure 7B:
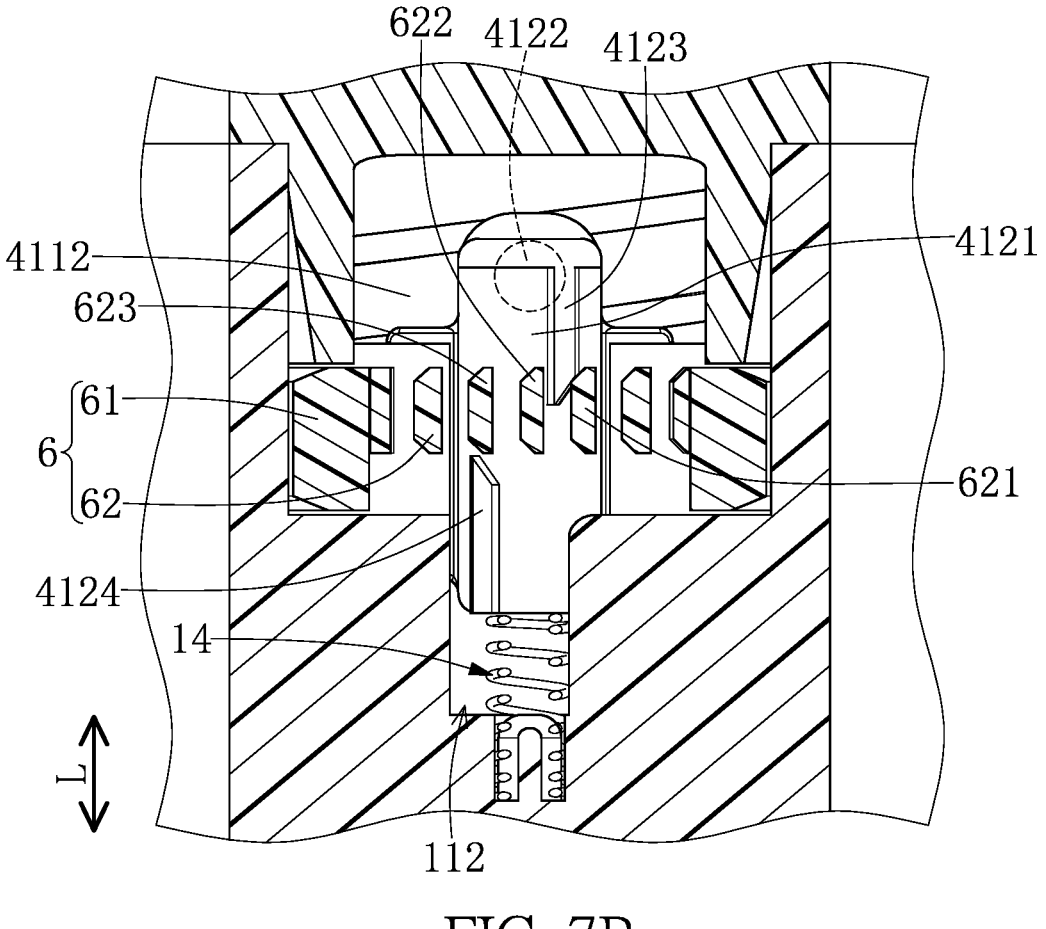
FIG. 7B is a schematic view showing a movement of the nebulizer after that of FIG. 7A.
Figure 7C:
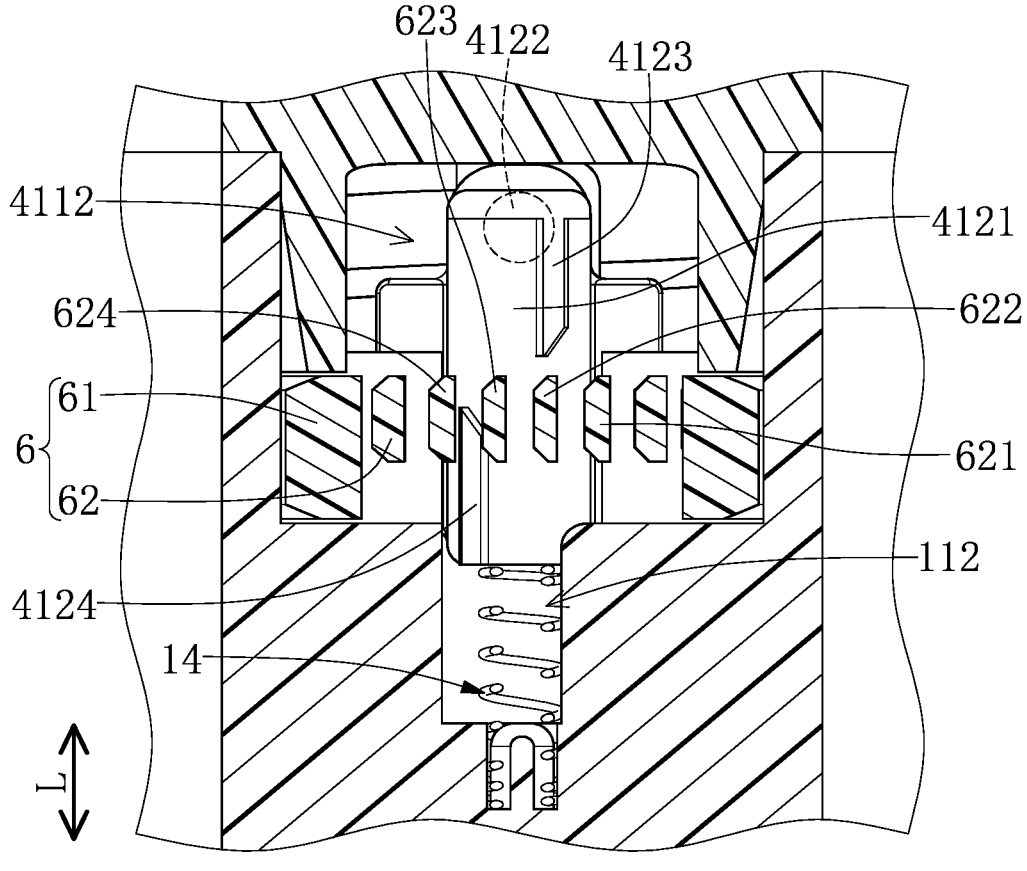
FIG. 7C is a schematic view showing a movement of the nebulizer after that of FIG. 7B.
Figure 8:
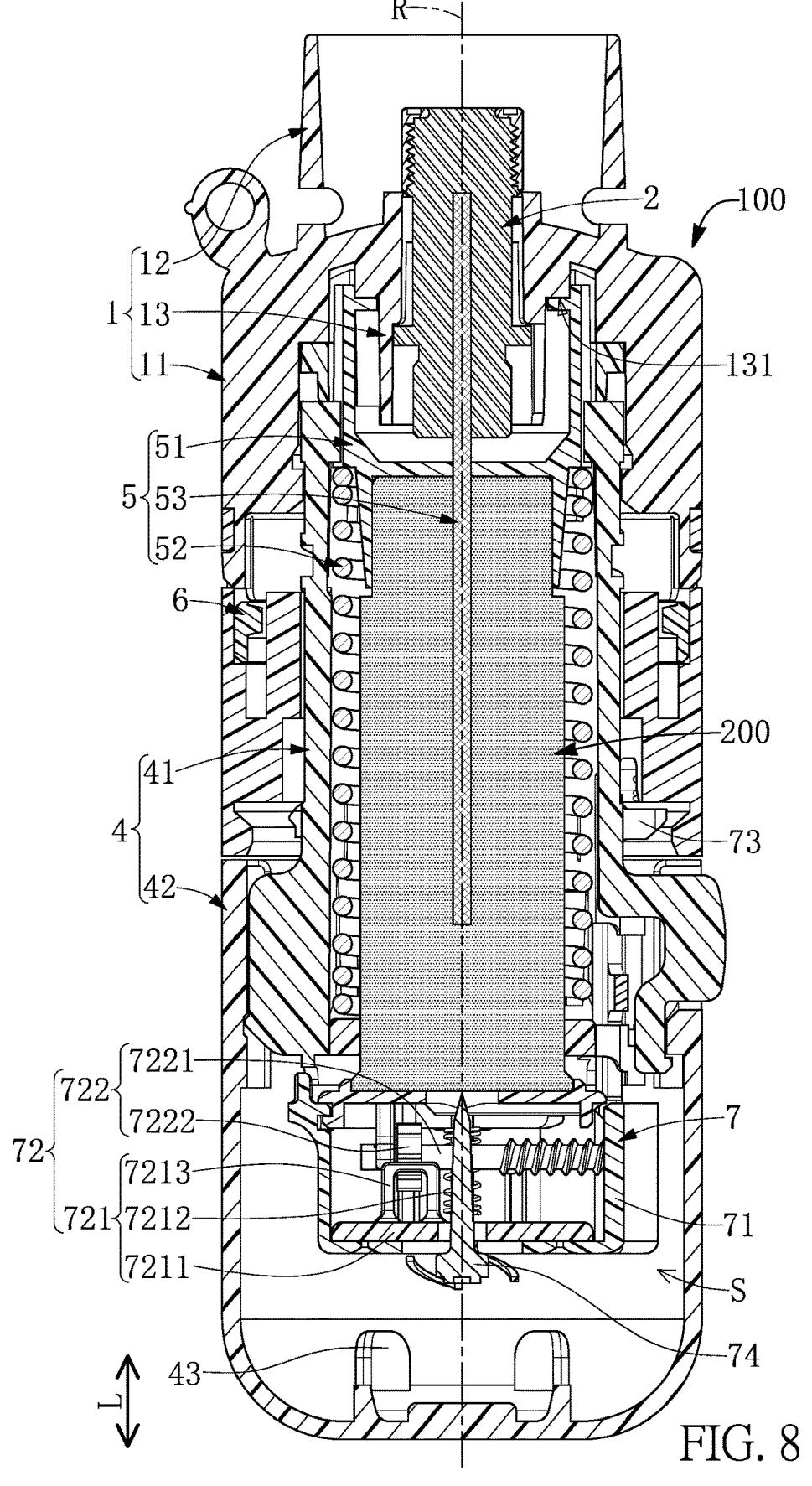
FIG. 8 is a cross-sectional view taken along line VIII-VIII of FIG. 1.
Figure 9:
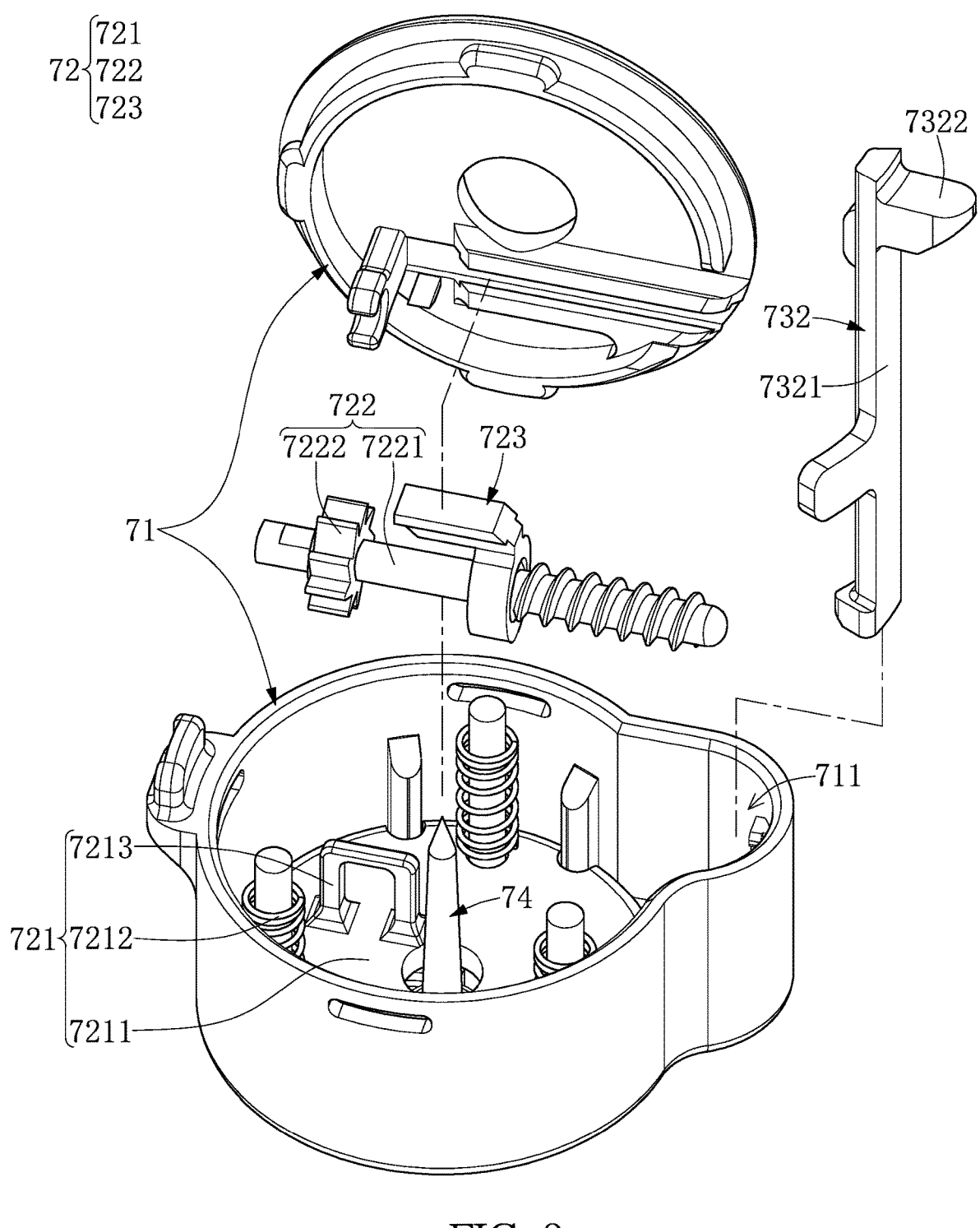
FIG. 9 is an exploded view of a locking module of the nebulizer according to the first embodiment of the present disclosure.

In other words, when the rotating module 4 is rotated by the predetermined angle (e.g., when the linking module 5 is moved from the initial position shown in FIG. 3 to the standby position shown in FIG. 4), the tube 411 presses the driving block 412 through the rail slot 4111, so that the driving block 412 is moved along (the rail slot 4111 and) the straight direction L (as shown in FIG. 7A to FIG. 7C) by being limiting from the limiting slot 112. The returning elastic member 14 is located on a movement path of the driving block 412, and the driving block 412 abuts against the returning elastic member 14.

Specifically, as shown in FIG. 3 to FIG. 6, the predetermined angle is 360/N degrees, and N is a positive integer greater than one and is a factor of three hundred and sixty. The rail slot 4111 includes N number of spiral slots 4112 arranged along the rotation axis R and N number of connection slots 4113 that are parallel to the straight direction L. Moreover, head ends of the N number of the spiral slots 4112 are located at a same height with respect to the rotation axis R, tail ends of the N number of the spiral slots 4112 are also located at a same height with respect to the rotation axis R, and the head end and the tail end, which are arranged adjacent to each other and respectively belonging to two of the spiral slots 4112, are in spatial communication with each other through one of the connection slots 4113. In the present embodiment, N is two, but the present disclosure is not limited thereto.

Accordingly, when the rotating module 4 is rotated by the predetermined angle (e.g., when the linking module 5 is moved from the initial position to the standby position), the driving block 412 located in one of the connection slots 4113 is adjusted to be located in another one of the connection slots 4113 through being pressed by the rotation of the spiral slot 4112.

Furthermore, the driving block 412 in the present embodiment includes a carrying board 4121, an inner protrusion 4122 connected to an inner surface of the carrying board 4121, a first protrusion 4123, and a second protrusion 4124, the latter two of which are connected to an outer surface of the carrying board 4121. The inner protrusion 4122 of the driving block 412 is movably assembled in the rail slot 4111, and the first protrusion 4123 and the second protrusion 4124 are in a staggered arrangement.

The counter 6 is located on the movement path of the driving block 412 and includes an annular body 61 and a plurality of gear teeth 612 that are formed on an inner surface of the annular body 61 and that are spaced apart from each other. The annular body 61 is partially exposed from the housing segment 11 for showing a rotation angle of the annular body 61 that can further present how many times of the atomization process have been implemented by the nebulizer 100.

When the rotating module 4 is rotated by the predetermined angle (e.g., when the linking module 5 is moved from the initial position shown in FIG. 3 to the standby position shown in FIG. 4), the driving block 412 of the rotating module 41 can push at least one of the gear teeth 62 so as to drive the counter 6 to be rotated by a counting angle (as shown in FIG. 7A to FIG. 7C). Moreover, after the driving block 412 pushes at least one of the gear teeth 62, the returning elastic member 14 can push the driving block 412 to be moved to an original position along the straight direction L.

Specifically, as shown in FIG. 5 and FIG. 7A, when the linking module 5 is located at the initial position, the first protrusion 4123 faces toward one of the gear teeth 62 (hereafter refer to a first gear tooth 621) along the straight direction L, and the second protrusion 4124 is inserted into a gap between another two of the gear teeth (hereafter respectively refer to a second gear tooth 622 and a third gear tooth 623) adjacent to each other.

As shown in FIG. 6 and FIG. 7B, as the linking module 5 is moved from the initial position toward the standby position, the driving block 412 is downwardly moved along the straight direction L through being pressed by one of the spiral slots 4112, so that the first protrusion 4123 of the driving block 412 is inserted into a gap between the first gear tooth 621 and the second gear tooth 622, and the second protrusion 4124 faces toward the third gear tooth 623 along the straight direction L.

As shown in FIG. 7C, when the linking module 5 is located at the standby position, the driving block 412 is upwardly moved along the straight direction L by being driven from the returning elastic member 14, so that the second protrusion 4124 is inserted into a gap between the third gear tooth 623 and an adjacent fourth gear tooth 624, and the first protrusion 4123 faces toward the second gear tooth 622 along the straight direction L.

Accordingly, the counter 6 of the nebulizer 100 provided by the present embodiment is in cooperation with the casing 1 and the rotating module 4 through structural design thereof, so that the counter 6 can show the usage count of the nebulizer 100 through the counting angle, and the user can intuitively obtain a current status of the nebulizer 100.

Locking Function of Nebulizer According to the First Embodiment

The above description describes the counting function of the nebulizer 100 of the present embodiment, and the following description describes a locking function of the nebulizer 100 of the present embodiment. Moreover, a specific structure of the nebulizer 100 for the locking function can be adjusted or changed according to design requirements, so that the following description of the present embodiment only describes one of possible structures of the nebulizer 100, but the present disclosure is not limited thereto.

As shown in FIG. 8 to FIG. 10C, the casing 1 has a locking slot 113 that is recessed in an inner surface of the housing segment 11 and that extends along the straight direction L. The rotating module 4 in the present embodiment includes a pusher 43 assembled to an inner bottom of the cover 42. The pusher 43 in the present embodiment is integrally formed on and erectly connected to the inner bottom of the cover 42, but the present disclosure is not limited thereto.

The locking module 7 is configured to be connected to the bottom of the container bottle 200 and is arranged in the interior space S. In the present embodiment, the locking module 7 includes a box body 71 configured to be connected to the bottom of the container bottle 200, a trigger mechanism 72 assembled in the box body 71 and corresponding in position to the pusher 43, and a locking mechanism 73 that is assembled to the rotating mechanism 41.

The box body 71 in the present embodiment is fixed to the bottom of the container bottle 200 in an undetachable manner, and the box body 71 has an opening 711 located on a movement path of the locking mechanism 73, but the present disclosure is not limited thereto. For example, in other embodiments of the present disclosure not shown in the drawings, the box body 71 can be fixed to the bottom of the container bottle 200 in a detachable manner according to design requirements.

The trigger mechanism 72 includes a driving member 721, a rotation member 722 arranged corresponding to the driving member 721, and a progressing member 723 that is connected to the rotation member 722. In the present embodiment, the driving member 721 includes a plate-like body 7211, a spring 7212 abutting against the box body 71 and the plate-like body 7211, and a hook 7213 that is (erectly) formed on the plate-like body 7211. The plate-like body 7211 is disposed on a bottom of the box body 71 and corresponds in position to the pusher 43, the spring 7212 tends to push the plate-like body 7211 toward the bottom of the box body 71, and the hook 7213 that corresponds in position to the rotation member 722.

The rotation member 722 includes a screw rod 7221 pivotally connected to the box body 71 and a plurality of teeth 7222 that are disposed on the screw rod 7221. The teeth 7222 are disposed on the screw rod 7221 in an annular arrangement and are preferably a ratchet gear, the progressing member 723 is slidably disposed on the box body 71 and is threadedly engaged with the screw rod 7221, and the rotation member 722 can drive the progressing member 723 to be moved (along the screw rod 7221) by rotation thereof.

In summary, each time the atomization process is completed by the nebulizer 100, the driving member 721 (e.g., the box body 7211) is configured to be pressed and moved by the pusher 43 (e.g., the pusher 43 presses the plate-like body 7211 by passing through the bottom of the box body 71) in a manner that rotates the screw rod 7221 by driving at least one of the teeth 7222 to move, such that the progressing member 723 is then driven to be moved (along the screw rod 7221 and in a direction away from the teeth 7222).

In other words, each time the atomization process is completed by the nebulizer 100, the locking module 7 moves back and forth along the rotation axis R once, so that the trigger mechanism 72 is moved toward the locking mechanism 73 through being pressed by the pusher 43. In the present embodiment, rotation of the screw rod 7221 is implemented in the following manner. Each time the atomization process is completed by the nebulizer 100, the plate-like body 7211 moves in the box body 71 back and forth once through the pusher 43 and the spring 7212, so that the hook 7213 rotates the screw rod 7221 by moving at least one of the teeth 7222.

Specifically, the locking mechanism 73 is assembled to the tube 411 of the rotating mechanism 41, and the locking mechanism 73 in the present embodiment includes an elastic member 731 and a locking rod 732. The elastic member 731 is disposed in the locking slot 113 of the casing 1. The locking rod 732 has a rod body 7321 and a protruding portion 7322 that (perpendicularly) extends from the rod body 7321. Moreover, the rod body 7321 (slidably) assembled to the tube 411 (along the straight direction L) and corresponds in position to (e.g., faces toward) the opening 711 of the box body 71, and the protruding portion 7322 corresponds in position to (e.g., faces toward) the locking slot 113 of the casing 1.

Figure 10A:
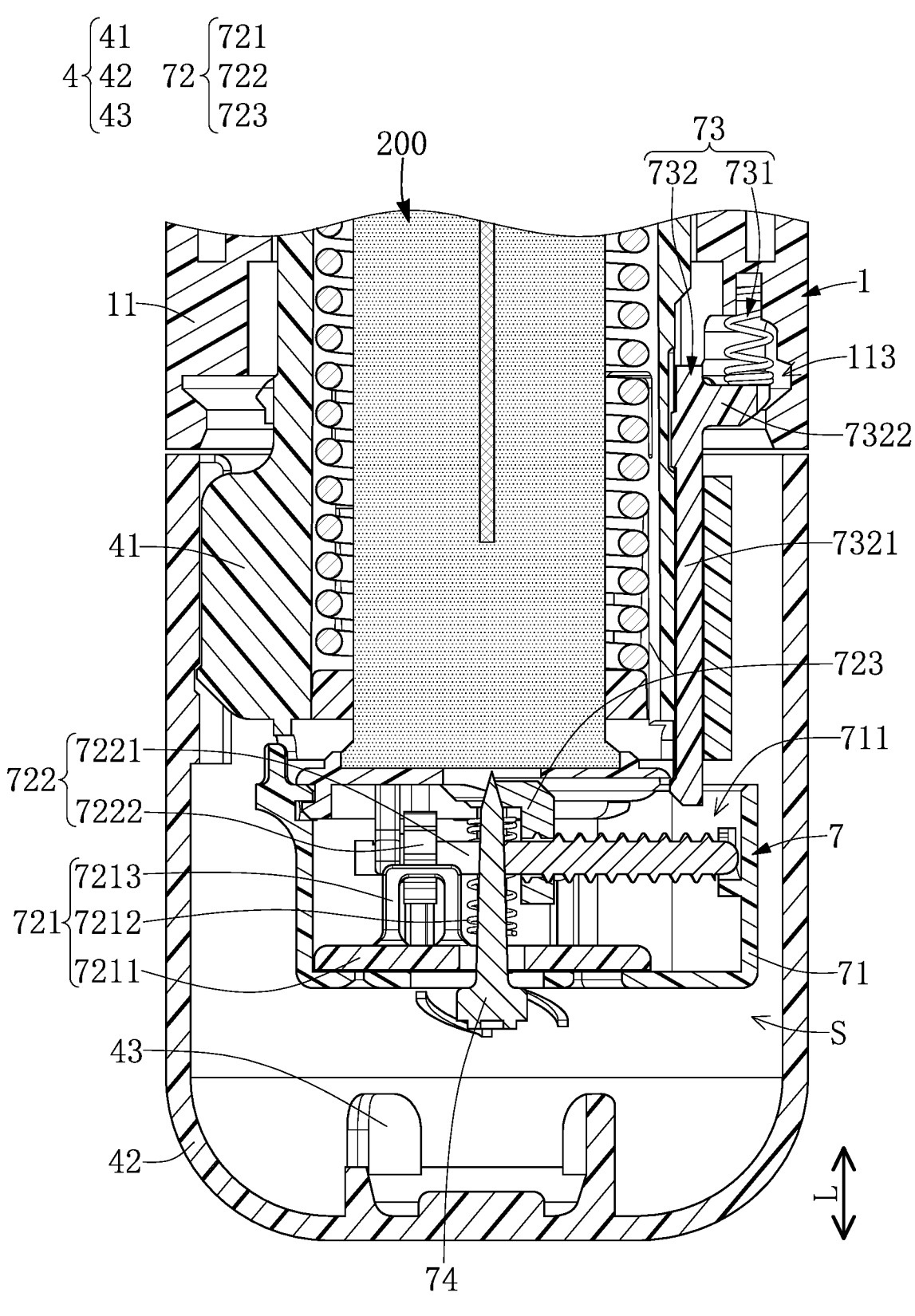
FIG. 10A is a cross-sectional view taken along line XA-XA of FIG. 1.
Figure 10B:
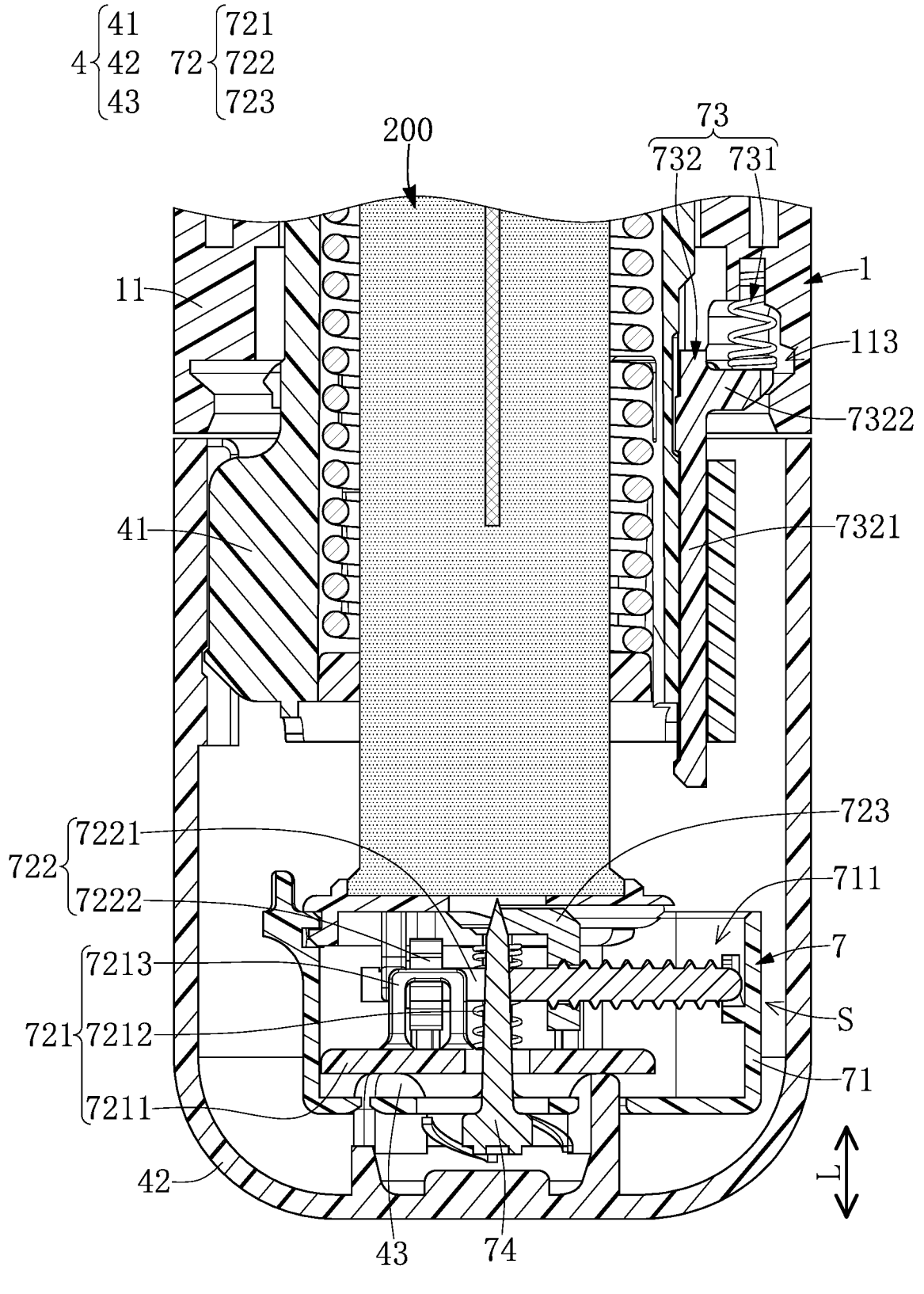
FIG. 10B is a schematic view showing a movement of the nebulizer after that of FIG. 10A.
Figure 10C:
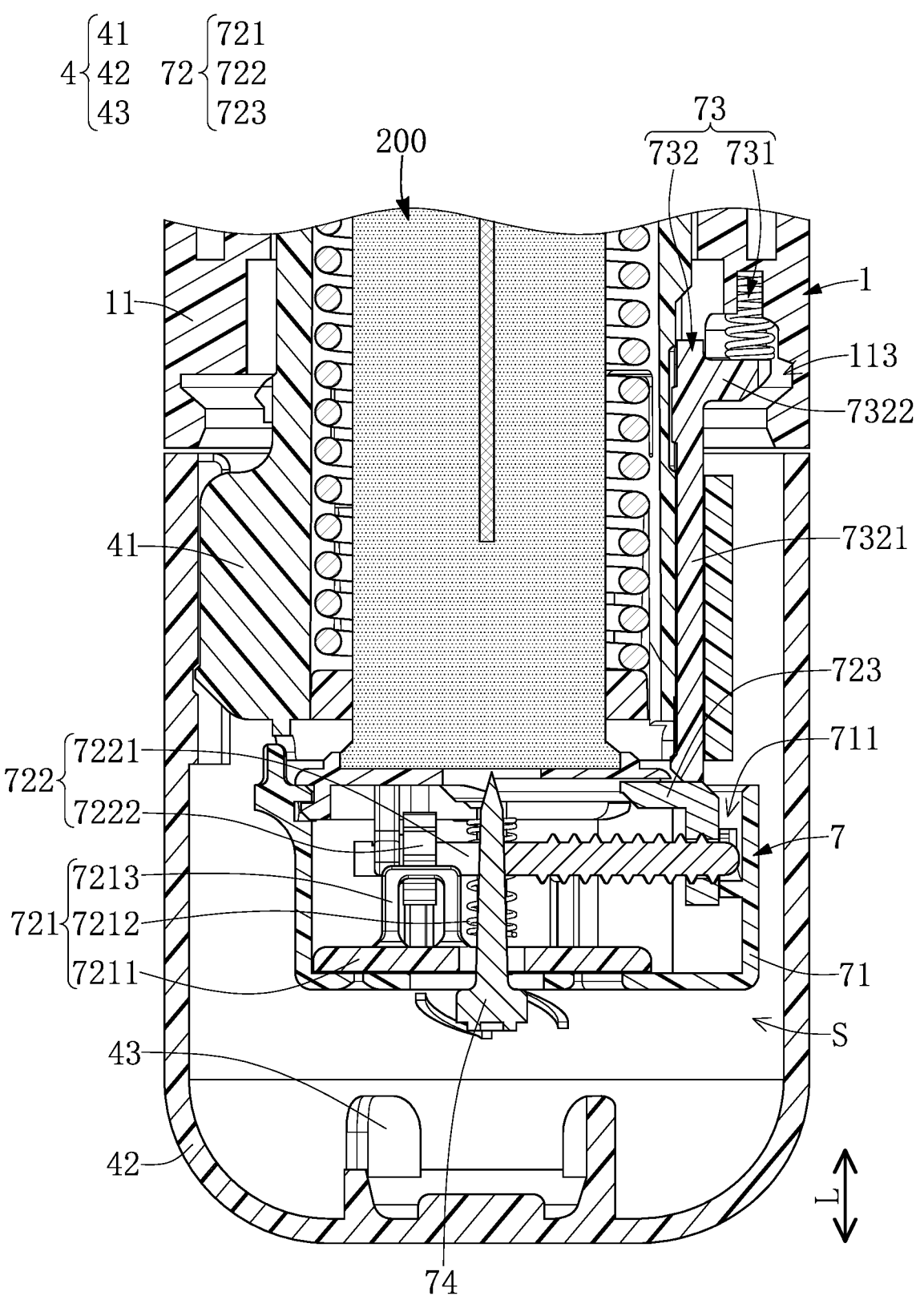
FIG. 10C is a schematic view showing a movement of the nebulizer after that of FIG. 10B.

As shown in FIG. 10A to FIG. 10C, when the nebulizer 100 completes a predetermined number of times of the atomization process, the trigger mechanism 72 pushes the locking mechanism 73, so that the locking mechanism 73 is moved toward the casing 1 and is limited in position to restrict a rotation of the rotating mechanism 41. Specifically, when the nebulizer 100 completes the predetermined number of times of the atomization process, the progressing member 723 is driven by the rotation member 722 until the locking mechanism 73 is moved by the progressing member 723 (e.g., the progressing member 723 is driven by the rotation member 722 until the opening 711 is closed off by the progressing member 723 and the locking mechanism 73 is pushed by the progressing member 723), so that the locking mechanism 73 is moved to the casing 1 and limited in position.

In the present embodiment, the locking mechanism 73 is limited in the following manner. When the nebulizer 100 completes the predetermined number of times of the atomization process, the rod body 7321 is moved by the progressing member 723, so that the protruding portion 7322 moves into the locking slot 113 and presses the elastic member 731 for limiting a rotation of the rotating module 4. In other words, before the nebulizer 100 completes the predetermined number of times of the atomization process, a bottom end of the rod body 7321 is located in the opening 711, and the protruding portion 7322 is located outside of the locking slot 113 and is in contact with the elastic member 731.

In addition, the locking mechanism 73 further includes a pricking needle 74 erectly assembled to the box body 71. The pricking needle 74 can be pressed to prick into the bottom of the container bottle 200 by passing through a top of the box body 71, thereby maintaining an interior pressure of the container bottle 200 to be equal to an external atmospheric pressure, but the present disclosure is not limited thereto.

Accordingly, the locking module 7 of the nebulizer 100 provided by the present embodiment is in cooperation with the casing 1 and the rotating module 4 through structural design thereof, so that after the nebulizer 100 completes the predetermined number of times of the atomization process, the locking module 7 (e.g., the protruding portion 7322) can restrict the rotation of the rotating module 4 for preventing the nebulizer 100 from using the container bottle 200 to be assembled therein.

Second Embodiment

Figure 11:
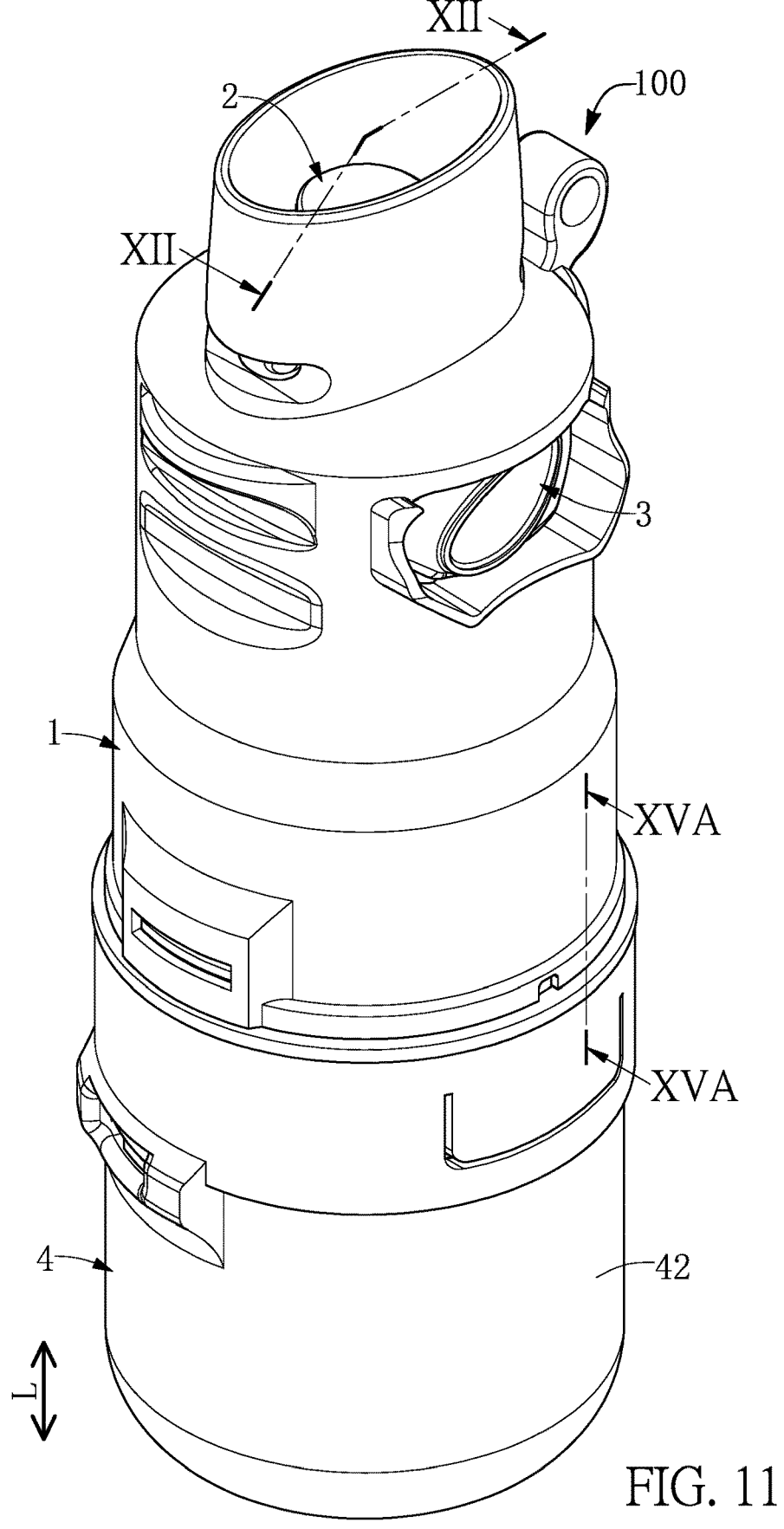
FIG. 11 is a perspective view of the nebulizer according to a second embodiment of the present disclosure.
Figure 20A:
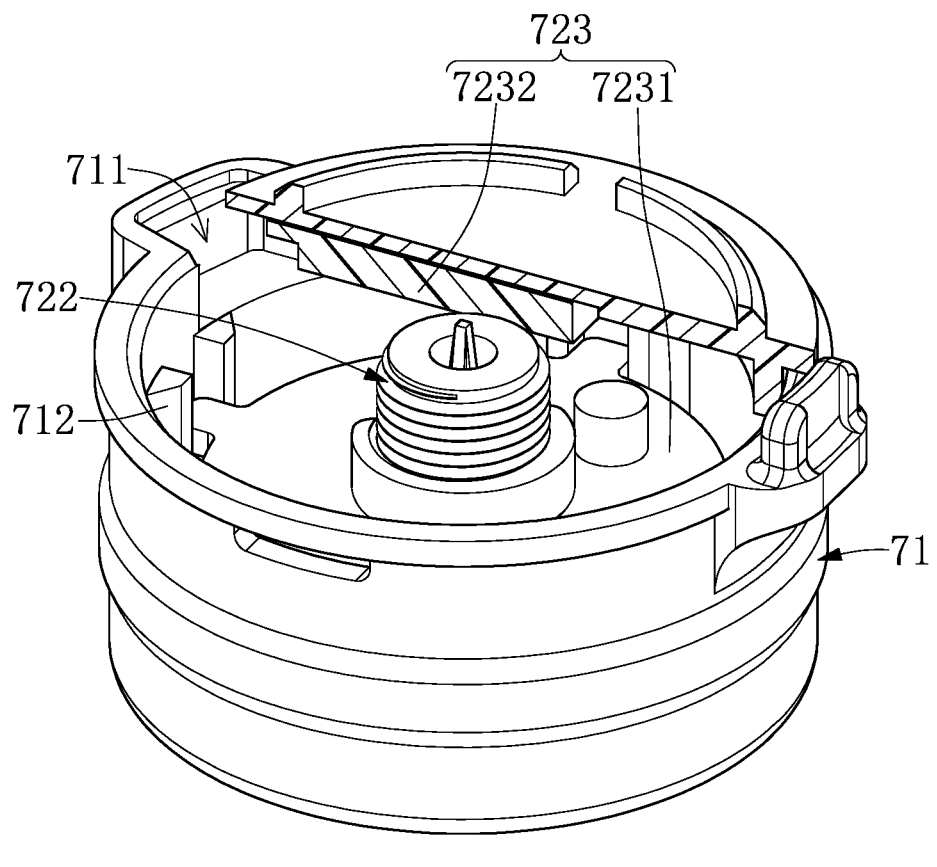
FIG. 20A is a perspective cross-sectional view showing an initialized assembly part of the locking module of the nebulizer according to the second embodiment of the present disclosure.
Figure 20B:
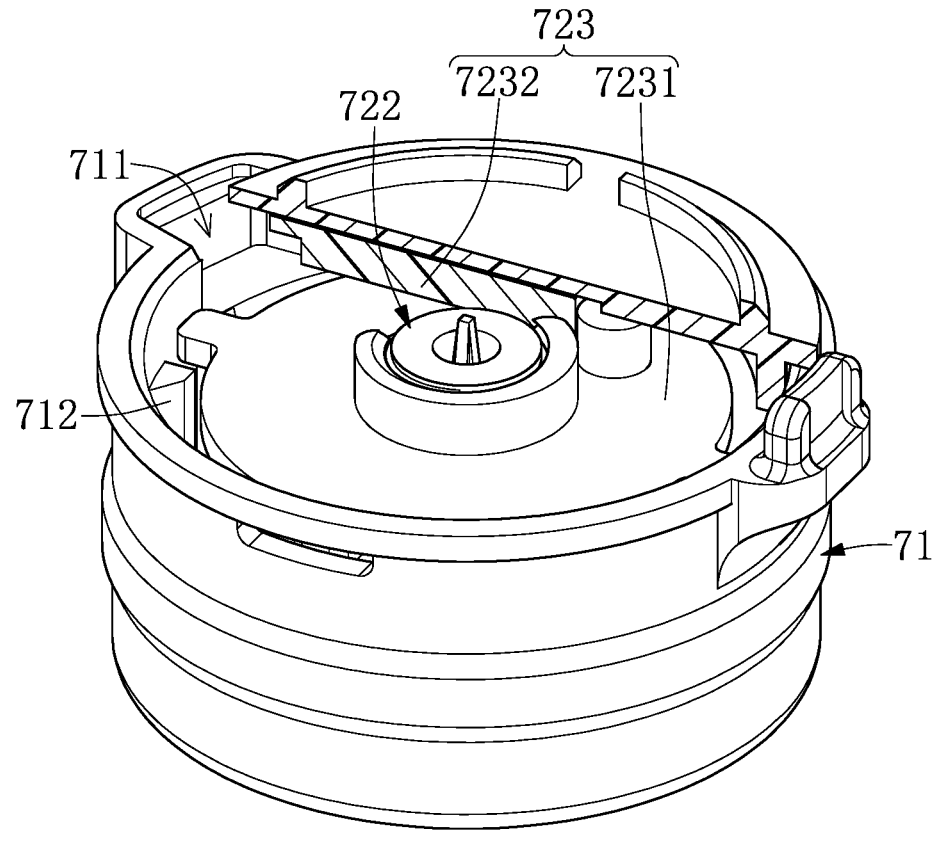
FIG. 20B is a schematic view showing a movement of the locking module after that of FIG. 20A.
Figure 20C:
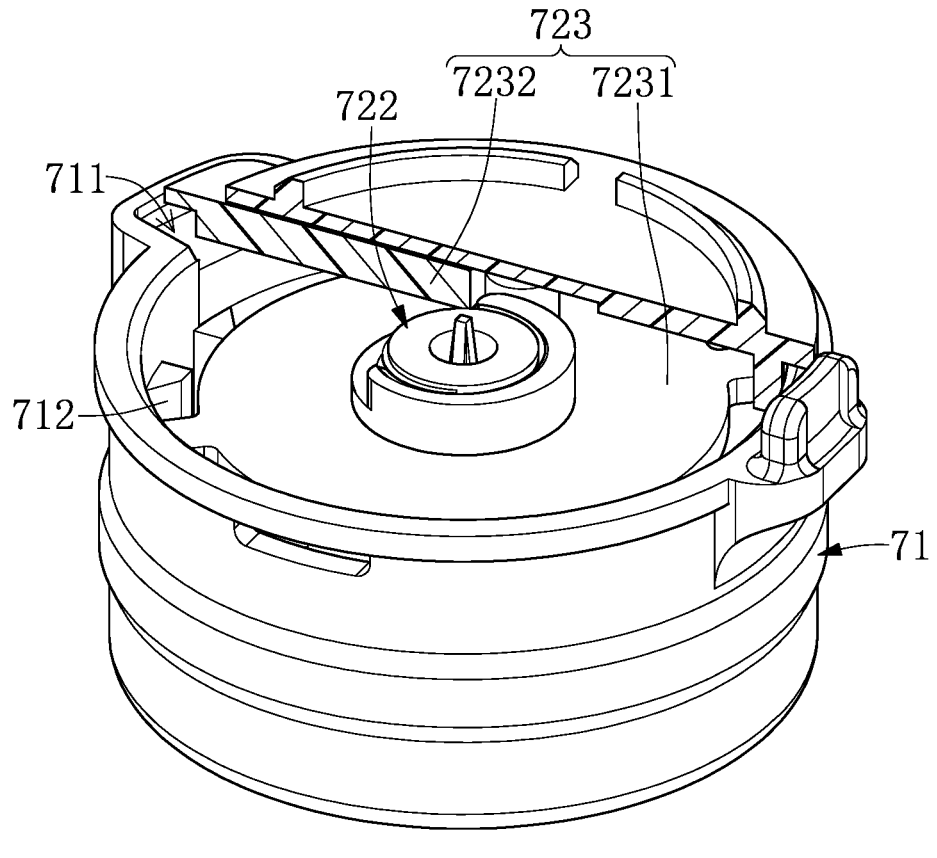
FIG. 20C is a schematic view showing a movement of the locking module after that of FIG. 20B.

Referring to FIG. 11 and FIG. 20C, a second embodiment of the present disclosure, which is similar to the first embodiment of the present disclosure, is provided. For the sake of brevity, descriptions of the same components in the first and second embodiments of the present disclosure (e.g., the basic configuration of the nebulizer 100) will be omitted herein, and the main difference between the second embodiment and the first embodiment is as follows: structure of the nebulizer 100 in the present embodiment is provided for implementing the counting function and the locking function, and the nebulizer 100 in the present embodiment further has an initializing function.

Counting Function of Nebulizer According to the Second Embodiment

Figure 12:
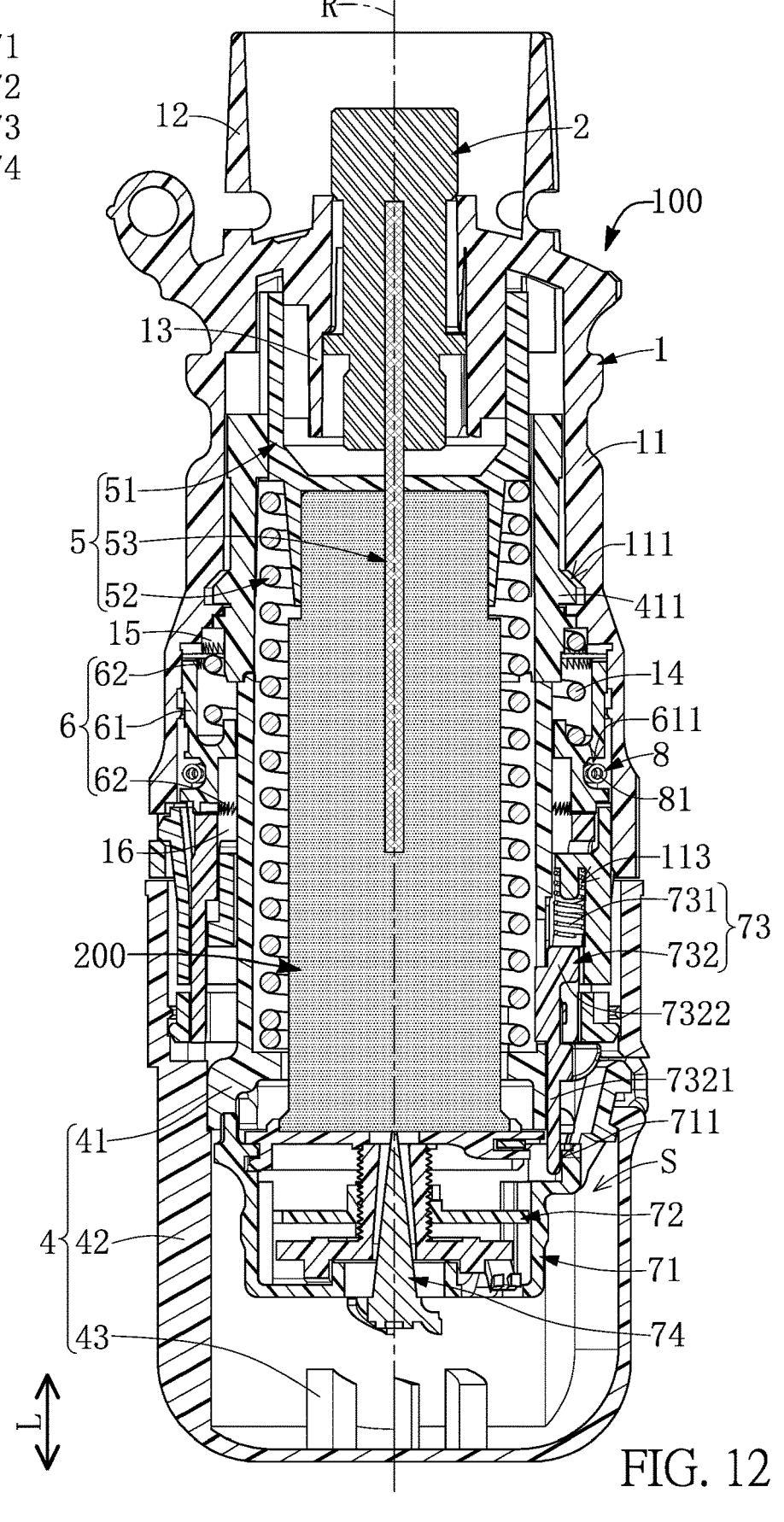
FIG. 12 is a cross-sectional view taken along line XII-XII of FIG. 11.
Figure 13:
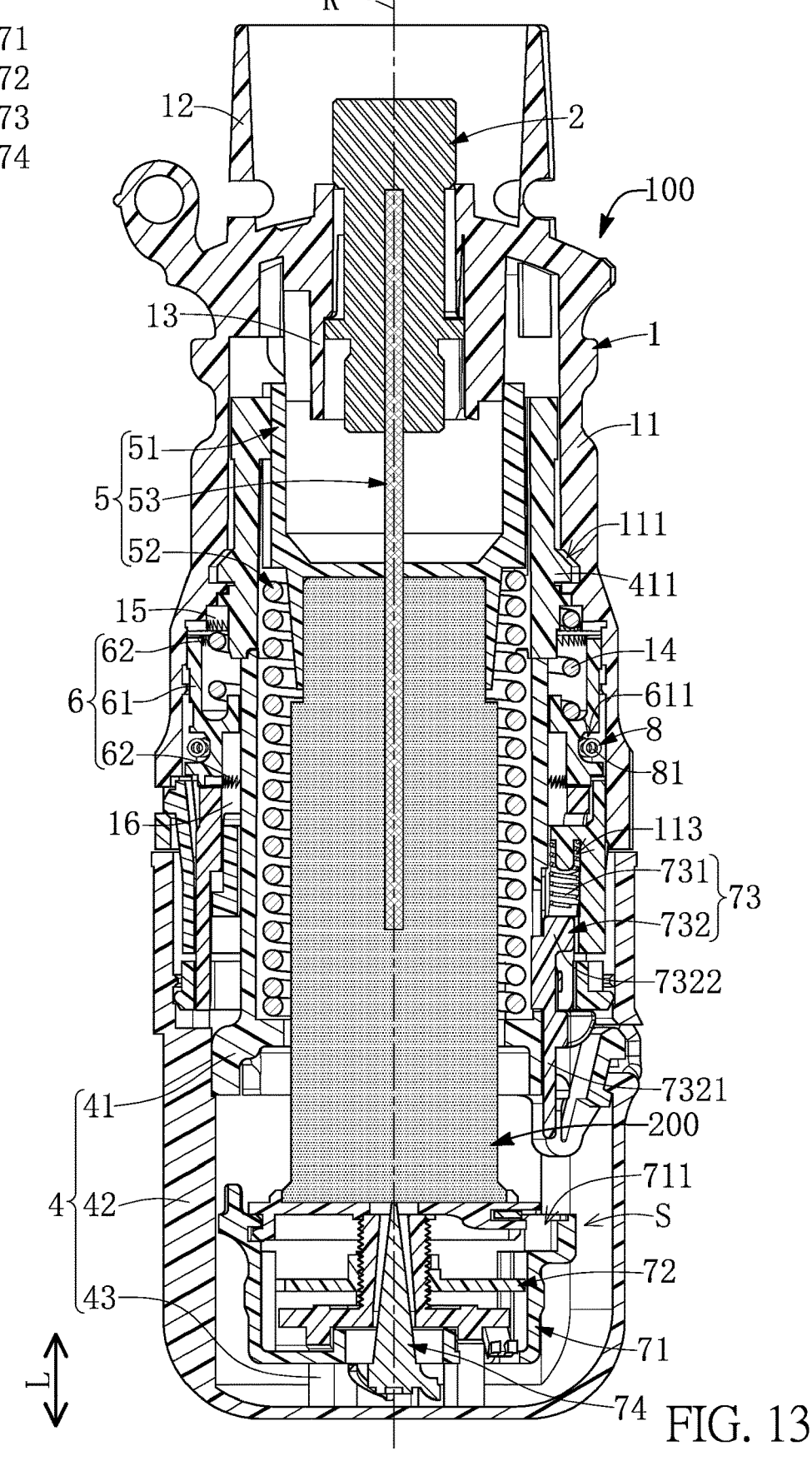
FIG. 13 is a cross-sectional view showing the nebulizer of FIG. 12 at the standby position.
Figure 15A:
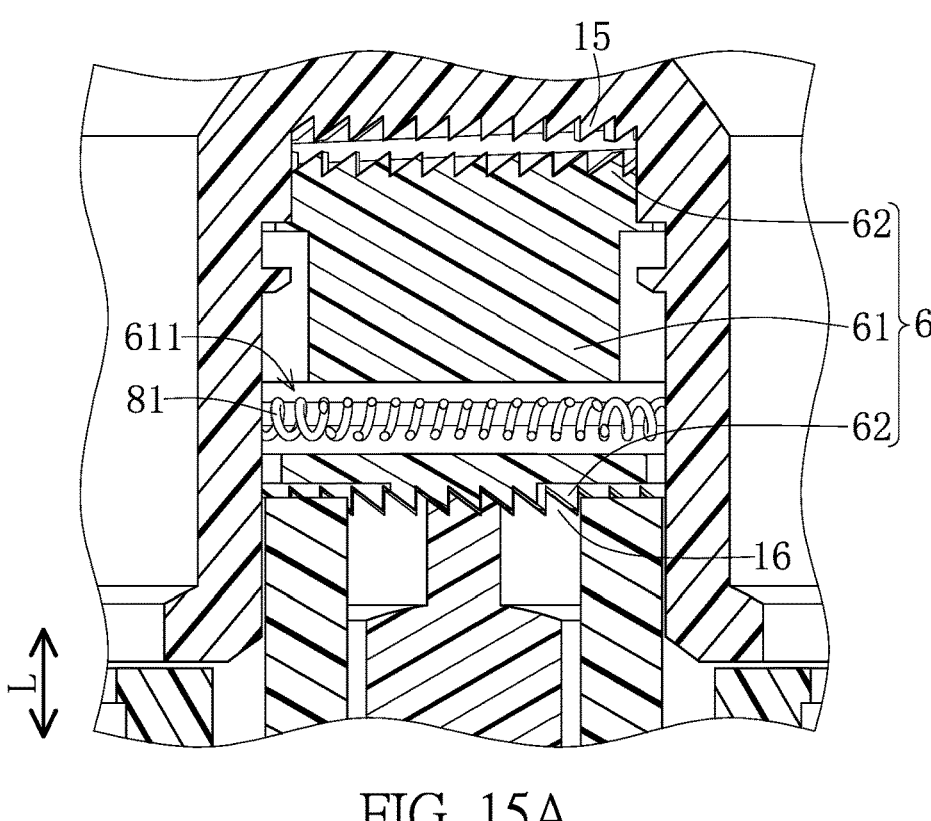
FIG. 15A is a cross-sectional view taken along line XVA-XVA of FIG. 11.
Figure 15B:
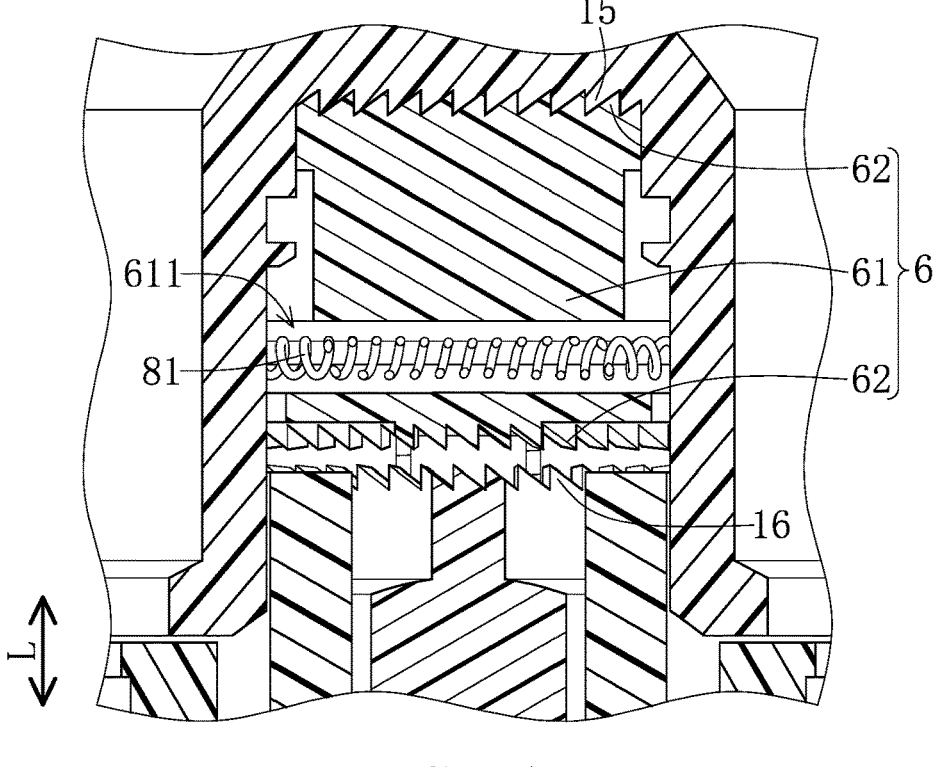
FIG. 15B is a schematic view showing a movement of the nebulizer after that of FIG. 15A.

As shown in FIG. 11 to FIG. 13, the casing 1 has a first annular rack 15 and a second annular rack 16. The first annular rack 15 and the second annular rack 16 face to each other along the straight direction L, and teeth of the first annular rack 15 and teeth of the second annular rack 16 are staggered with each other and are reverse arrangement (as shown in FIG. 15A and FIG. 15B). For example, a projection region defined by orthogonally projecting any one of the teeth of the first annular rack 15 along the straight direction L onto the second annular rack 16 covers (or is overlapped with) two of the teeth of the second annular rack 16 adjacent to each other.

Figure 14A:
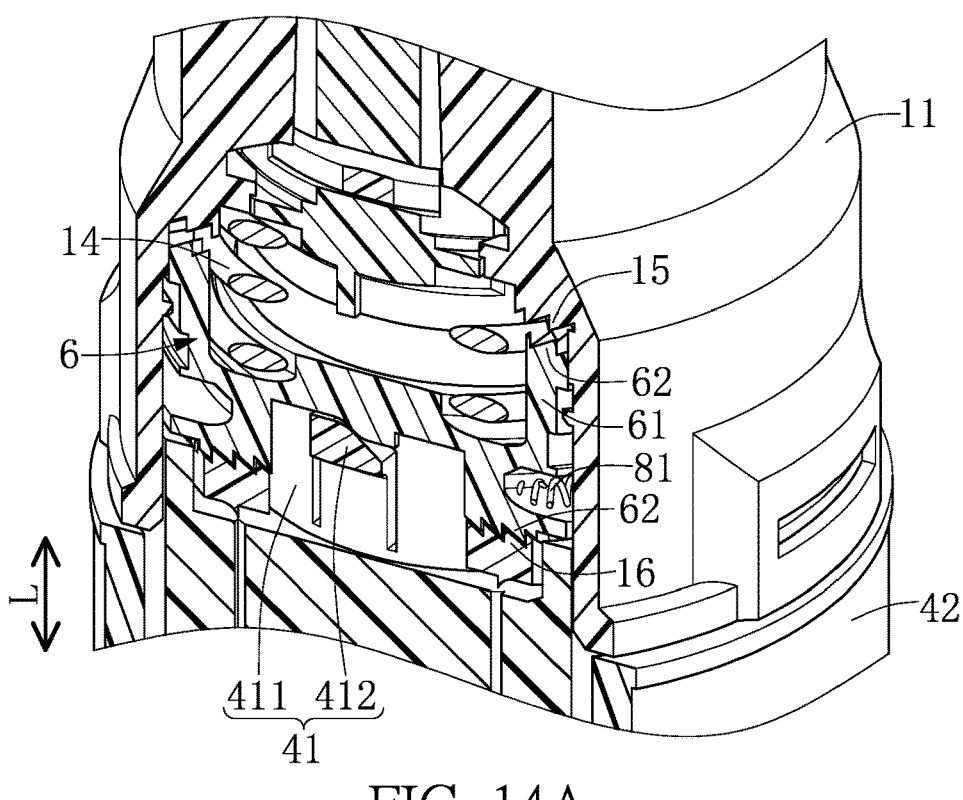
FIG. 14A is a perspective cross-sectional view showing a part of the nebulizer according to the second embodiment of the present disclosure.
Figure 14B:
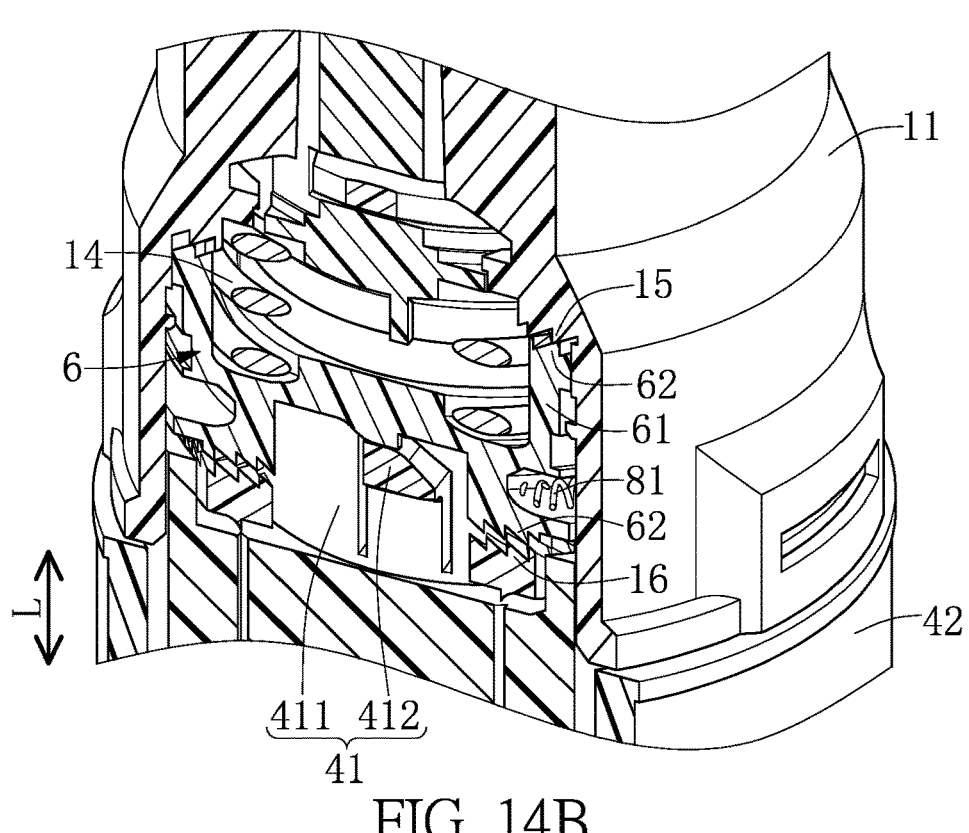
FIG. 14B is a schematic view showing a movement of the nebulizer after that of FIG. 14A.

As shown in FIG. 12 and FIG. 14A, the casing 1 includes a returning elastic member 14 arranged therein. The returning elastic member 14 in the present embodiment is a spring that can be elastically compressed along the straight direction L. The returning elastic member 14 is fixed to the housing segment 11 and the counter 6, and the returning elastic member 14 tends to drive the counter 6 to be moved toward the second annular rack 16.

The rotating mechanism 41 includes a tube 411 and a driving block 412. One end of the tube 411 (e.g., a top end of the tube 411 shown in FIG. 12) is engaged in the annular slot 111 of the housing segment 11, and another end of the tube 411 (e.g., a bottom end of the tube 411 shown in FIG. 12) is assembled to the cover 42. The driving block 412 is formed on the tube 411 (e.g., the driving block 412 protrudes from an outer surface of the tube 411).

As shown in FIG. 14A to FIG. 15B, (a part of) the counter 6 is located on the movement path of the driving block 412, and the counter 6 is substantially in a ring-shape and includes an annular body 61 and a plurality of gear teeth 612. The annular body 61 is partially exposed from the housing segment 11 for showing a rotation angle of the annular body 61 that can further present how many times of the atomization process implemented by the nebulizer 100.

Moreover, the gear teeth 612 of the counter 6 respectively face toward and correspond in shape to the teeth of the first annular rack 15 and the teeth of the second annular rack 16. In the present embodiment, the gear teeth 612 are respectively arranged on two ends of the counter 6 (e.g., a top end and a bottom end of the counter 6 shown in FIG. 15A and FIG. 15B) and are respectively arranged in two loops. The gear teeth 62 of the counter 6 arranged in the two loops respectively face toward and correspond in shape to the teeth of the first annular rack 15 and the teeth of the second annular rack 16.

In summary, when the rotating module 4 is rotated by the predetermined angle (e.g., when the linking module 5 is moved from the initial position shown in FIG. 12 to the standby position shown in FIG. 13), the driving block 412 of the rotating module 41 can (indirectly) push at least one of the gear teeth 62 so as to drive the counter 6 to be rotated by a counting angle. Specifically, when the rotating module 4 is rotated by the predetermined angle, the driving block 412 presses (the part of) the counter 6 to cause the counter 6 to be moved along the straight direction L, and the gear teeth 62 are moved along the teeth of the first annular rack 15 and the teeth of the second annular teeth 16 in turn so as to result a rotation of the counter 6.

Specifically, the gear teeth 62 can be moved along the first annular rack 15 by using the driving block 412 to move the counter 6. And then, after the gear teeth 62 are moved along the teeth of the first annular rack 15, the returning elastic member 14 can push the counter 6 to be moved toward the second annular rack 16 by abutting against the counter 6, so that the gear teeth 62 are moved along and are limited by the teeth of the second annular rack 16.

Initializing Function of Nebulizer According to the Second Embodiment

The above description describes the counting function of the nebulizer 100 of the present embodiment, and the following description describes the initializing function of the nebulizer 100 of the present embodiment that is in cooperation with the counting function. As shown in FIG. 12 and FIG. 16 to FIG. 18, the nebulizer 100 further includes an initializing assembly 8 assembled to the casing 1 and the counter 6. When the cover 42 is detached from the rotating mechanism 41, the cover 42 drives the initializing assembly 8, so that the counting angle of the counter 6 is deleted by the initializing assembly 8. Moreover, a specific structure of the nebulizer 100 for the initializing function can be adjusted or changed according to design requirements, so that the following description of the present embodiment only describes one of possible structures of the nebulizer 100, but the present disclosure is not limited thereto.

In the present embodiment, the initializing assembly 8 includes an initializing spring 81 having two ends respectively fixed to a part of the casing 1 and the counter 6. The cover 42 is engaged with the second annular rack 16. Accordingly, when the cover 42 is detached from the rotating mechanism 41, the cover 42 drives the second annular rack 16 (to move together and) to separate from the counter 6 (i.e., the counter 6 is not limited by the second annular rack 16), so that the initializing spring 81 tends to rotate the counter 6 to its original position by releasing an elastic force.

Specifically, the initializing spring 81 is substantially received in an annular groove 611 recessed in an outer surface of the annular body 61, one of the two ends of the initializing spring 81 is fixed to the annular body 61, and the other one of the two ends of the initializing spring 81 is fixed to the part of the casing 1 by extending outside of the annular groove 611.

Figure 16:
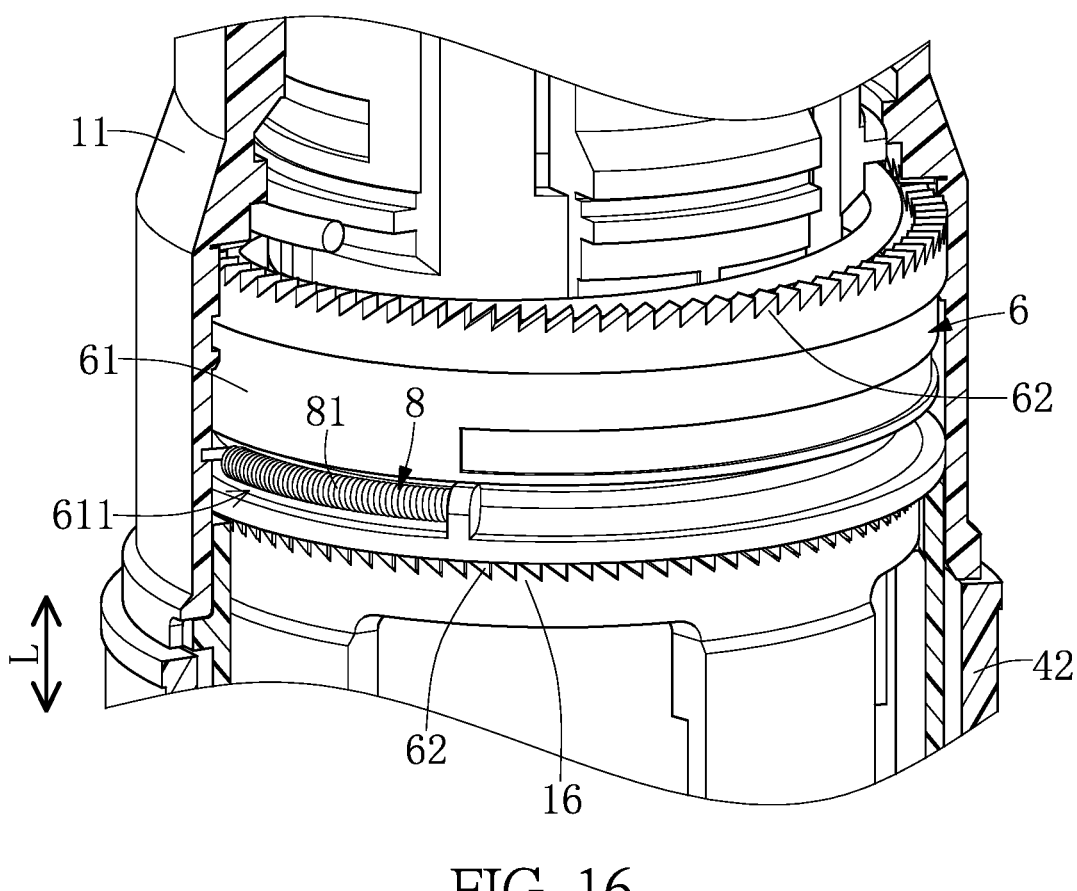
FIG. 16 is a perspective cross-sectional view showing an initialized assembly of the nebulizer according to the second embodiment of the present disclosure.
Figure 17:
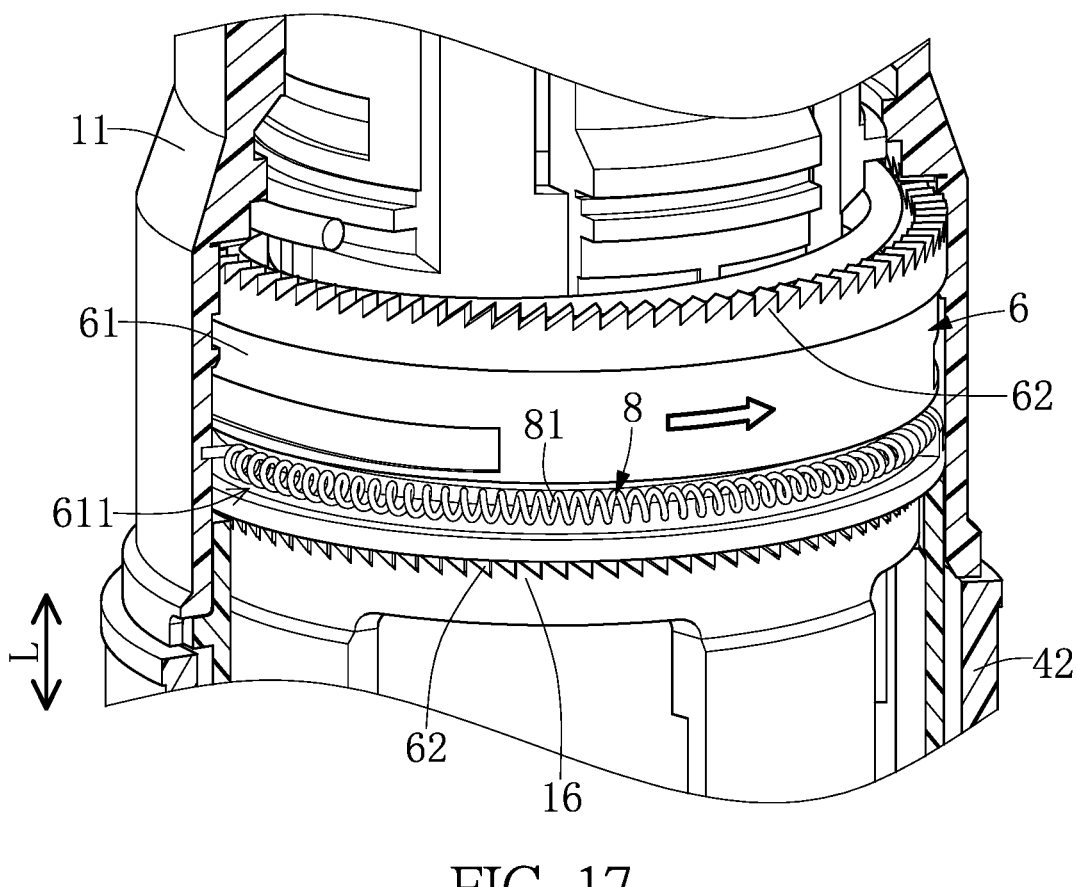
FIG. 17 is a schematic view showing a movement of the nebulizer after that of FIG. 16.
Figure 18:
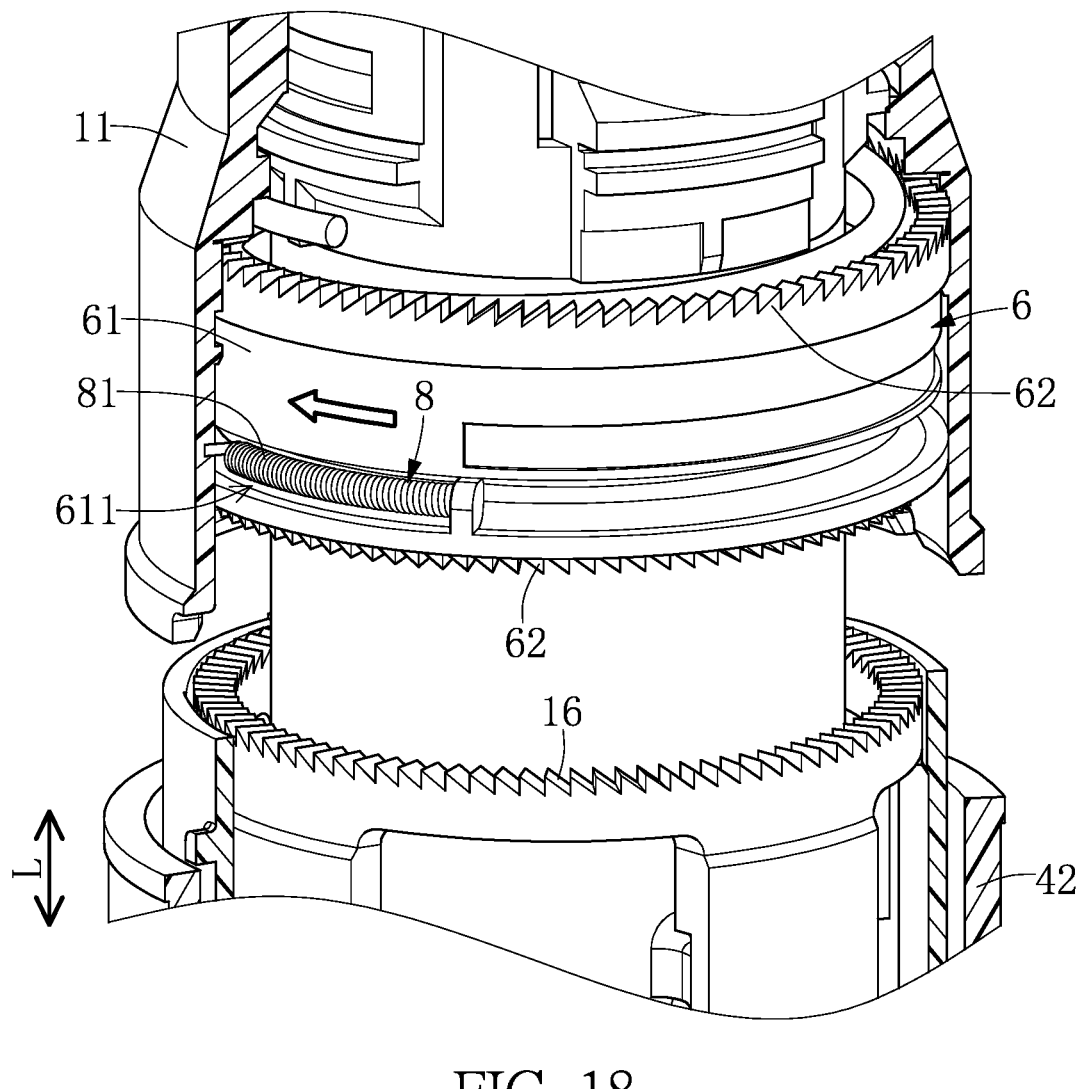
FIG. 18 is a schematic view showing a movement of the nebulizer after that of FIG. 17.
Figure 19:
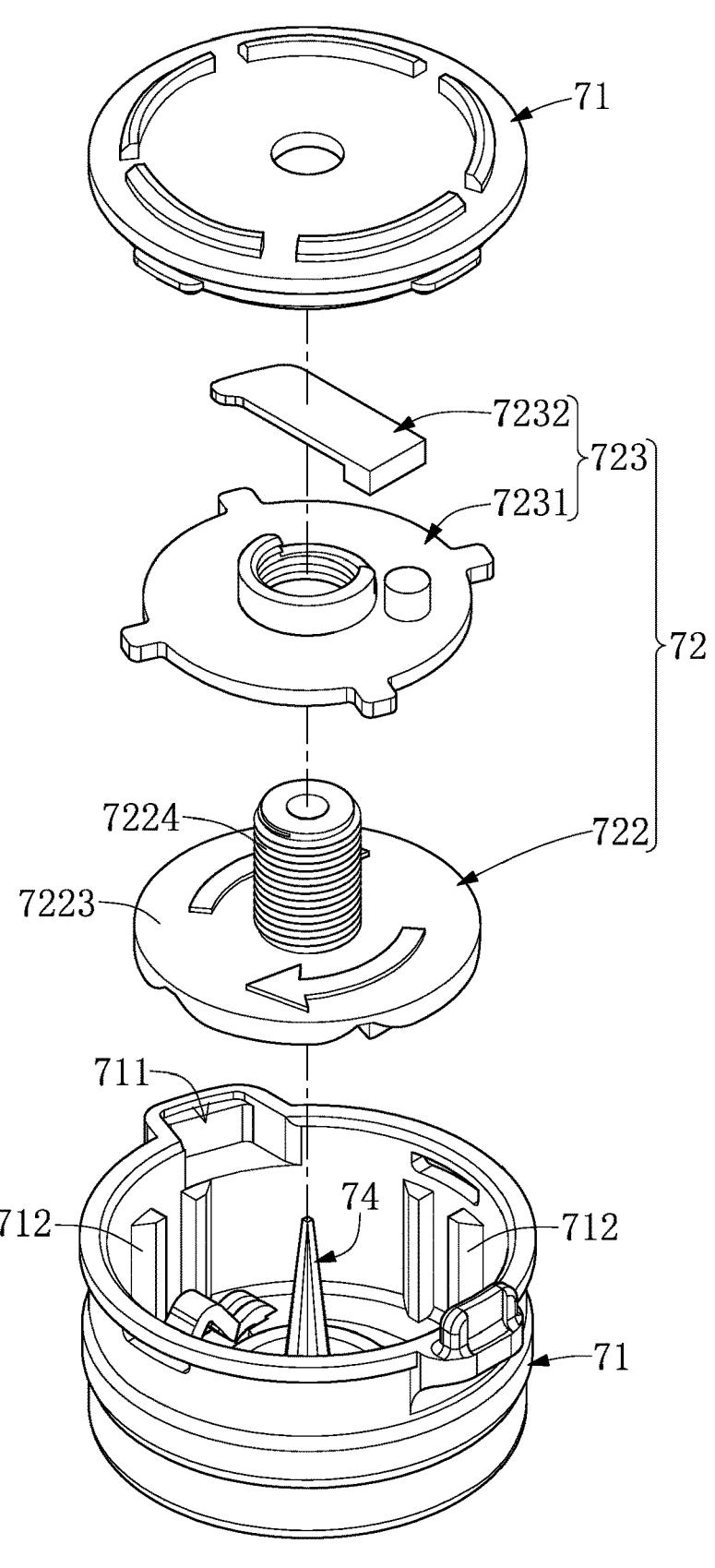
FIG. 19 is an exploded view of the locking module of the nebulizer according to the second embodiment of the present disclosure.

Accordingly, when the rotating module 4 is rotated by the predetermined angle (as shown in FIG. 16 and FIG. 17), the counter 6 is rotated by the counting angle and is limited by the second annular rack 16 (e.g., the counter 6 is not in contact with the first annular rack 15), so that the initializing spring 81 is stretched to store an elastic force. Moreover, when the cover 42 is detached from the rotating mechanism 41 (as shown in FIG. 18), the cover 42 drives another part of the casing 1 (e.g., the second annular rack 16) to separate from the counter 6 (and the counter 6 is not in contact with the first annular rack 15), so that the initializing spring 81 rotates the counter 6 to its original position by releasing the elastic force.

Accordingly, the initializing assembly 8 of the nebulizer 100 provided by the present embodiment is in cooperation with the casing 1 and the counter 6, so that the nebulizer 100 can reset the counting angle of at least one accumulated rotation of the counter 6 to zero through the cover 42, thereby providing the user with more diverse functions and facilitating the re-use of the nebulizer 100.

Locking Function of Nebulizer According to the Second Embodiment

The above description describes the initializing function of the nebulizer 100 of the present embodiment, and the following description describes the locking function of the nebulizer 100 of the present embodiment. Moreover, a specific structure of the nebulizer 100 for the locking function can be adjusted or changed according to design requirements, so that the following description of the present embodiment only describes one of possible structures of the nebulizer 100, but the present disclosure is not limited thereto.

The locking module 7 is configured to be connected to the bottom of the container bottle 200 and is arranged in the interior space S. In the present embodiment, the locking module 7 includes a box body 71 configured to be connected to the bottom of the container bottle 200, a trigger mechanism 72 assembled in the box body 71 and corresponding in position to the pusher 43, and a locking mechanism 73 that is assembled to the rotating mechanism 41. Each time the atomization process is completed by the nebulizer 100, the locking module 7 moves back and forth along the rotation axis R once, so that the trigger mechanism 72 is moved toward the locking mechanism 73 through being pressed by the pusher 43.

Specifically, the box body 71 in the present embodiment is fixed to the bottom of the container bottle 200 in an undetachable manner, the box body 71 has an opening 711 located on a movement path of the locking mechanism 73, and the box body 71 has a limiting structure 712 (e.g., a plurality of columns parallel to the straight direction L) formed on an inner lateral wall thereof, but the present disclosure is not limited thereto. For example, in other embodiments of the present disclosure not shown in the drawings, the box body 71 can be fixed to the bottom of the container bottle 200 in a detachable manner according to design requirements.

The trigger mechanism 72 includes a rotation member and a progressing member 723 that is connected to the rotation member 722. The rotation member 722 can drive the progressing member 723 to be moved by rotation thereof. In the present embodiment, the rotation member 722 includes a turntable 7223 corresponding in position to the pusher 43 and a stud 7224 that is erectly formed on the turntable 7223. The limiting structure 712 has a first height with respect to a bottom of the box body 71, and the first height is lower than a second height of the stud 7224 with respect to the bottom of the box body 71.

The progressing member 723 includes a progressing plate 7231 threadedly engaged with the stud 7224 and a progressing rod 7232 that is slidably disposed on a top of the box body 71. The progressing rod 7232 is separate from the progressing plate 7231. The turntable 7223 is rotatable through being pressed by the pusher 43 so as to drive the progressing plate 7231 to be moved along the stud 7224.

When the nebulizer 100 completes the predetermined number of times of the atomization process, the progressing plate 7231 is driven by the rotation member 722 until the progressing rod 7232 is moved by the progressing plate 7231, so that the progressing rod 7232 pushes the locking mechanism 73 to be moved toward the casing 1 and to be limited in position. Specifically, if the predetermined number is ten, when the progressing plate 7231 is located at a position lower than the first height (e.g., the first to seventh times of the atomization process), the progressing plate 7231 driven by the turntable 7223 is unable to be rotated by being limited from the limiting structure 712, and is only movable along the stud 7224 in a straight line (in a direction away from the turntable 7223); when the progressing plate 7231 is located at a position higher than the first height (e.g., the eighth to tenth times of the atomization process), a part of the progressing plate 7231 and the progressing rod 7232 are located at a same height, and the progressing plate 7231 is configured to be driven by the turntable 7223, so that the progressing plate 7231 and the turntable 7223 jointly rotate to push the progressing rod 7232.

Moreover, the locking mechanism 73 is assembled to the tube 411 of the rotating mechanism 41, and the locking mechanism 73 in the present embodiment includes an elastic member 731 and a locking rod 732. The elastic member 731 is disposed in the locking slot 113 of the casing 1. The locking rod 732 has a rod body 7321 and a protruding portion 7322 that (perpendicularly) extends from the rod body 7321. Furthermore, the rod body 7321 (slidably) assembled to the tube 411 (along the straight direction L) and corresponds in position to (e.g., faces toward) the opening 711 of the box body 71, and the protruding portion 7322 corresponds in position to (e.g., faces toward) the locking slot 113 of the casing 1.

In summary, when the nebulizer 100 completes a predetermined number of times of the atomization process, the trigger mechanism 72 pushes the locking mechanism 73, so that the locking mechanism 73 is moved toward the casing 1 and is then limited in position to restrict a rotation of the rotating mechanism 41. Specifically, when the nebulizer 100 completes the predetermined number of times of the atomization process, the progressing member 723 is driven by the rotation member 722 until the locking mechanism 73 is moved by the progressing member 723 (e.g., the progressing member 723 is driven by the rotation member 722 until the opening 711 is closed off by the progressing member 723 and the locking mechanism 73 is pushed by the progressing member 723), so that the locking mechanism 73 is moved to the casing 1 and limited in position.

In the present embodiment, the locking mechanism 73 is limited in the following manner. When the nebulizer 100 completes the predetermined number of times of the atomization process, the rod body 7321 is moved by the progressing member 723, so that the protruding portion 7322 moves into the locking slot 113 and presses the elastic member 731 for limiting a rotation of the rotating module 4. In other words, before the nebulizer 100 completes the predetermined number of times of the atomization process, a bottom end of the rod body 7321 is located in the opening 711, and the protruding portion 7322 is located outside of the locking slot 113 and is in contact with the elastic member 731.

In addition, the locking mechanism 73 further includes a pricking needle 74 erectly assembled to the box body 71. The pricking needle 74 can be pressed to prick into the bottom of the container bottle 200 by passing through a top of the box body 71, thereby maintaining an interior pressure of the container bottle 200 to be equal to an external atmospheric pressure, but the present disclosure is not limited thereto.

Accordingly, the locking module 7 of the nebulizer 100 provided by the present embodiment is in cooperation with the casing 1 and the rotating module 4 through structural design thereof, so that after the nebulizer 100 completes the predetermined number of times of the atomization process, the locking module 7 (e.g., the protruding portion 7322) can restrict the rotation of the rotating module 4 for preventing the nebulizer 100 from using the container bottle 200 assembled therein.

Third Embodiment

Figure 21:
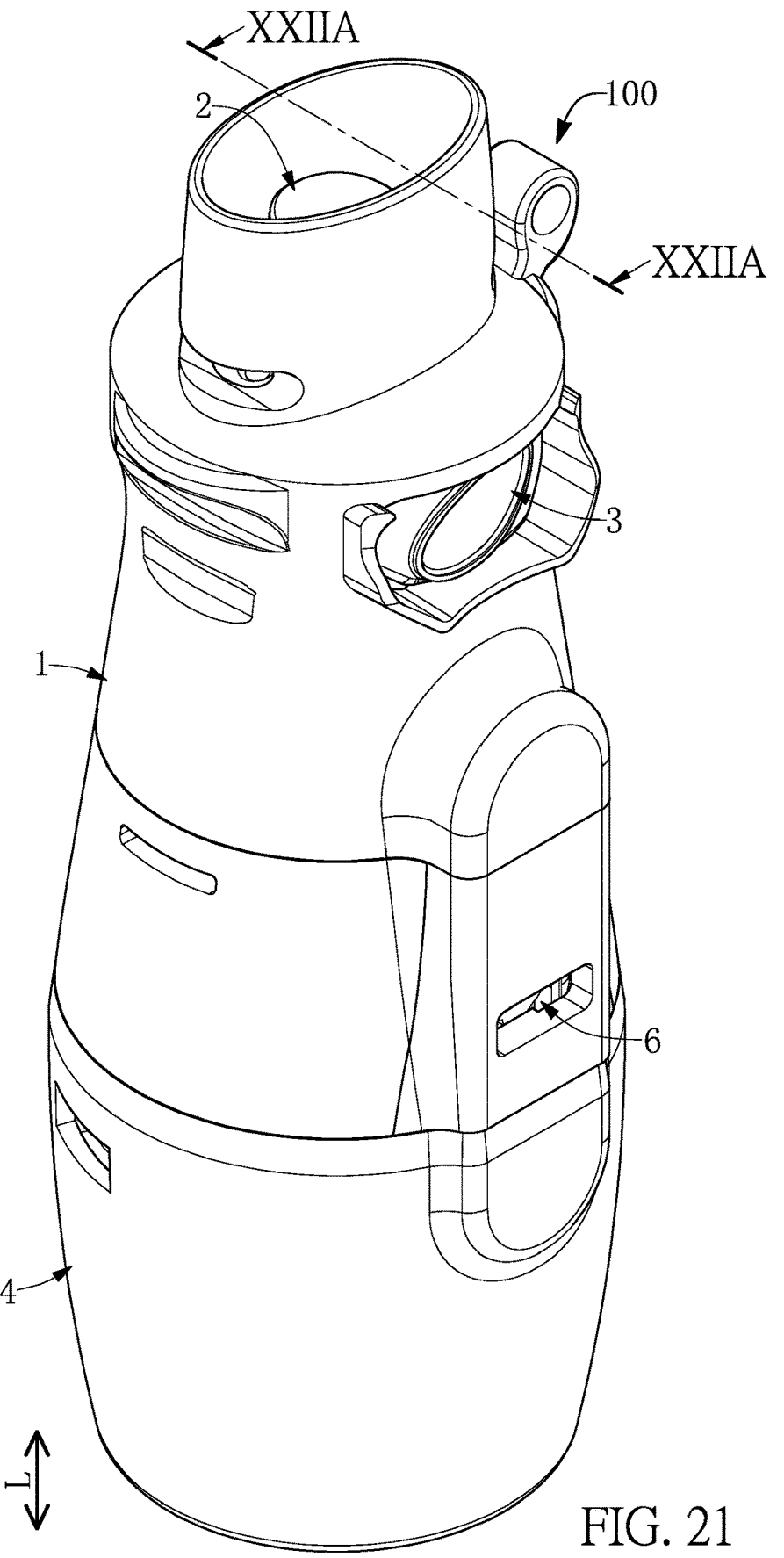
FIG. 21 is a perspective view of the nebulizer according to a third embodiment of the present disclosure.
Figure 25A:
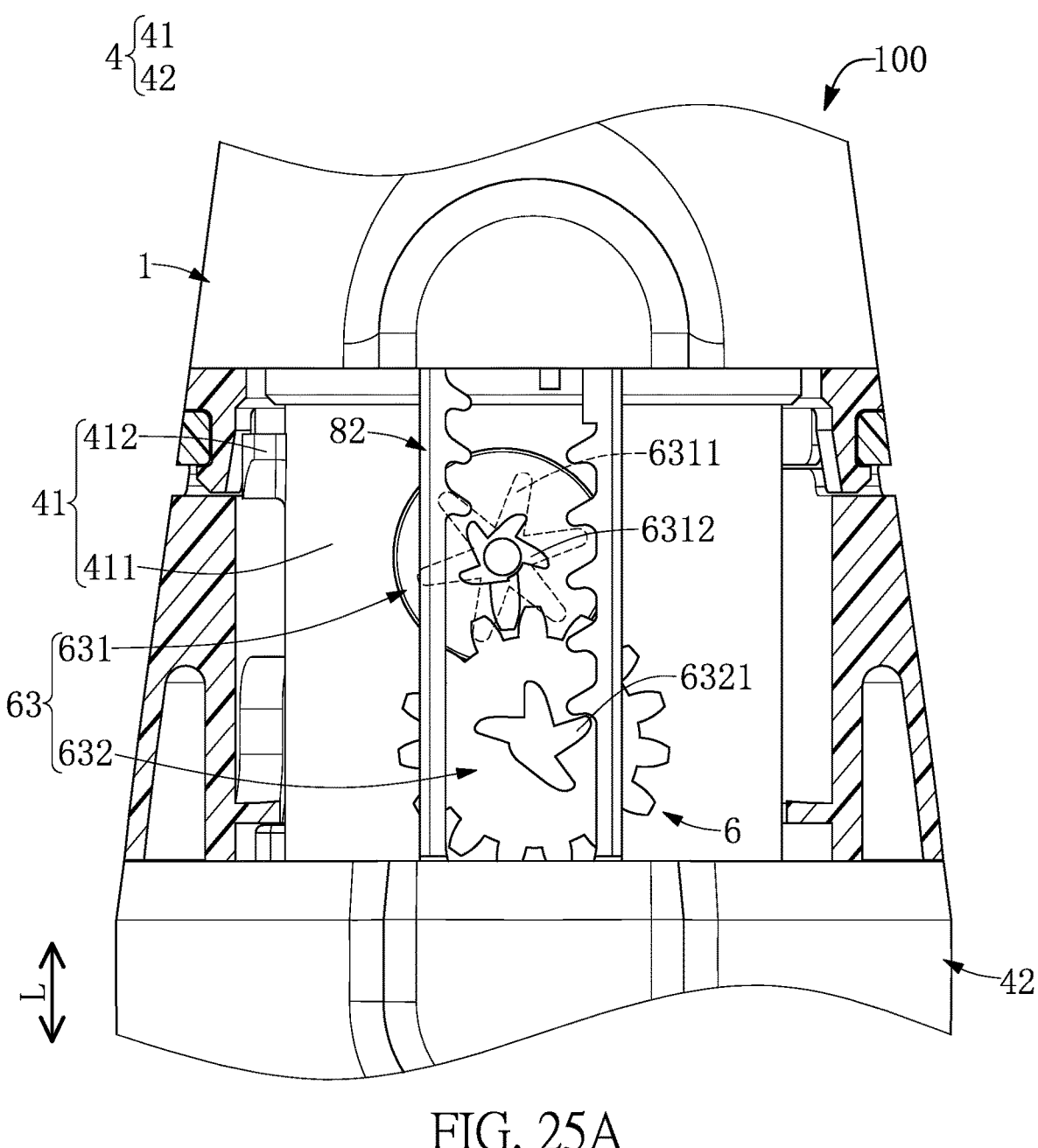
FIG. 25A is a cross-sectional view showing a part of the nebulizer according to a third embodiment of the present disclosure.
Figure 25B:
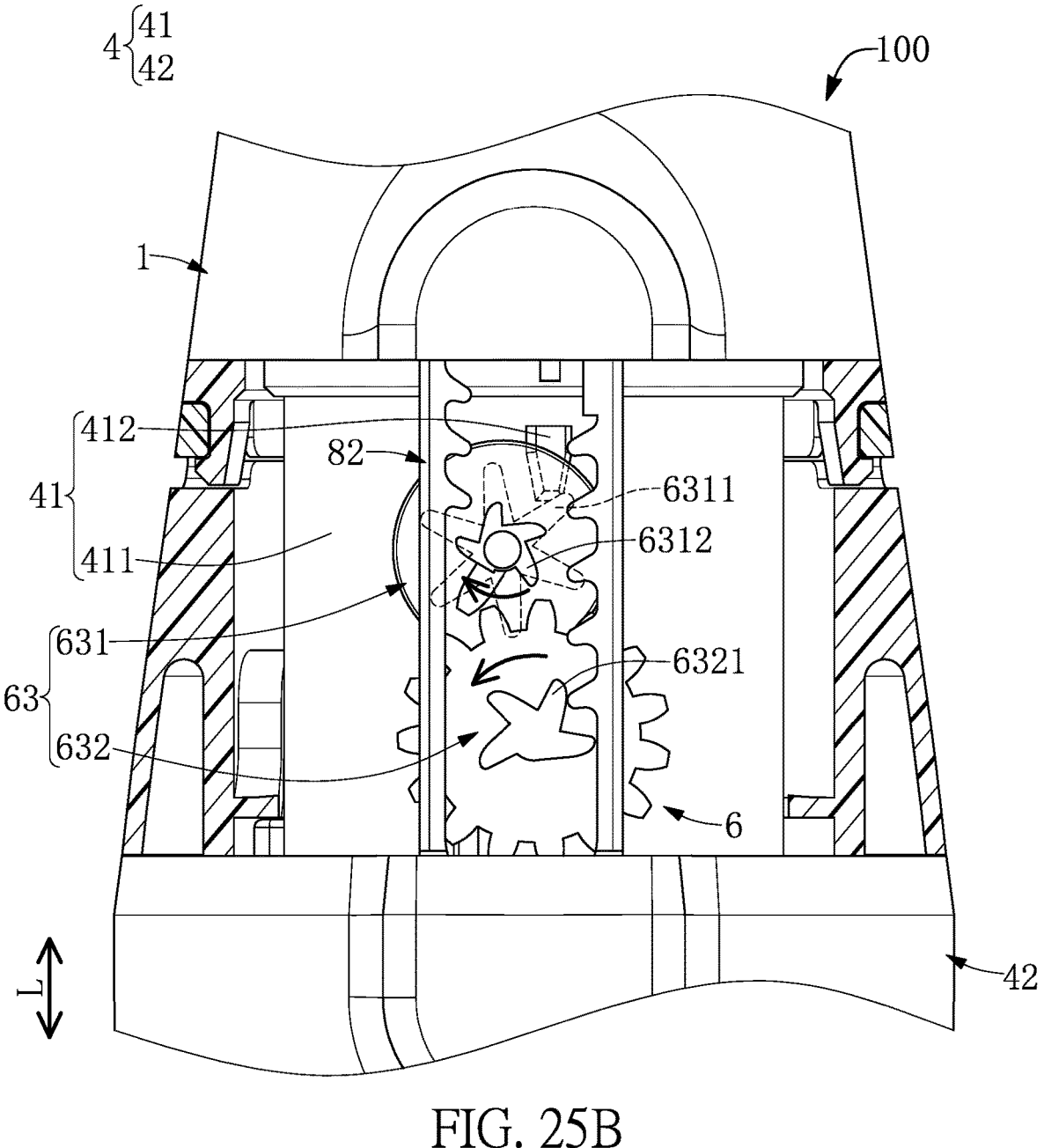
FIG. 25B is a schematic view showing a movement of the nebulizer after that of FIG. 25A.
Figure 25C:
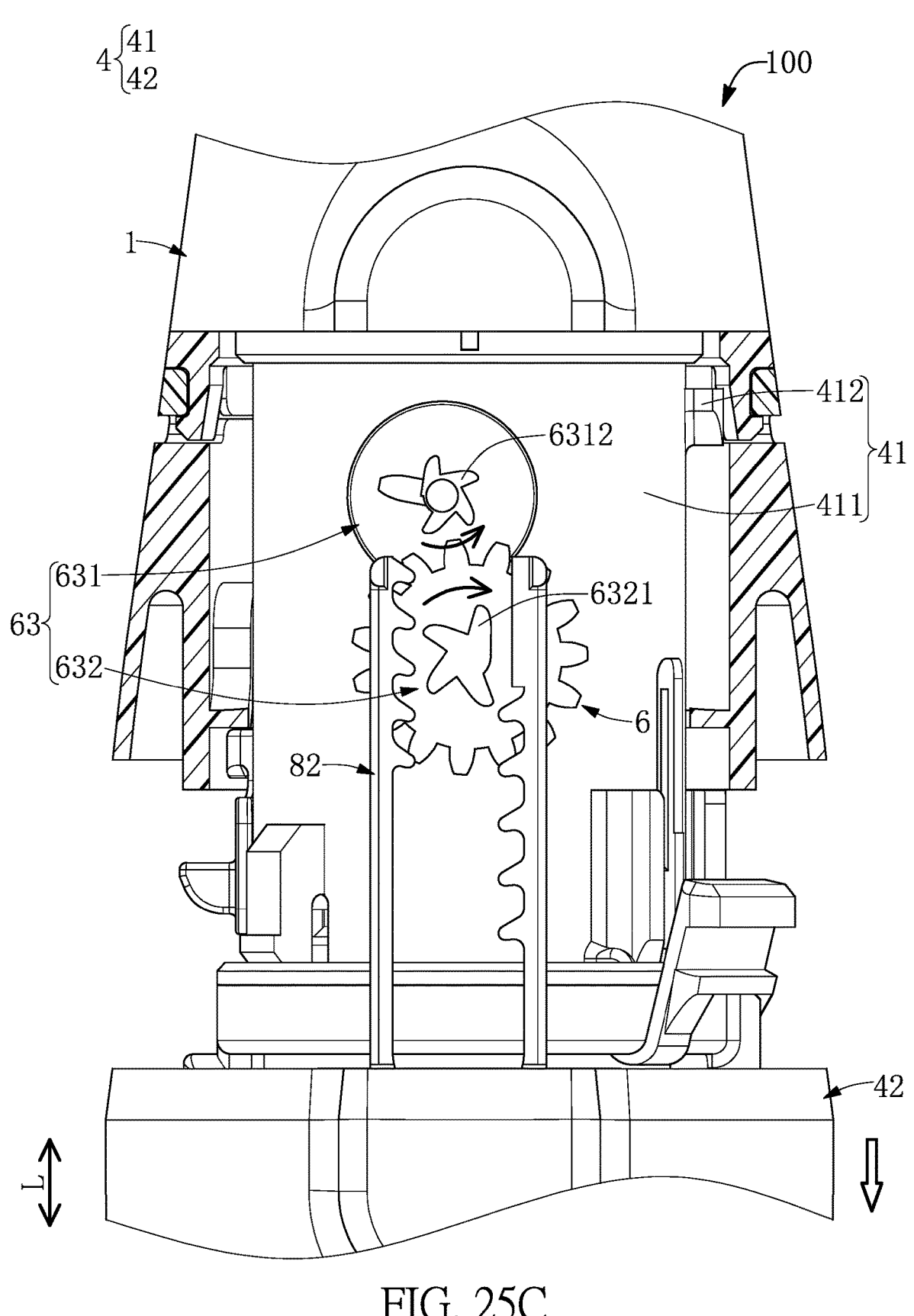
FIG. 25C is a schematic view showing a movement of the nebulizer after that of FIG. 25B.

Referring to FIG. 21 and FIG. 25C, a third embodiment of the present disclosure, which is similar to the second embodiment of the present disclosure, is provided. For the sake of brevity, descriptions of the same components in the second and third embodiments of the present disclosure (e.g., the basic configuration and the locking function of the nebulizer 100) will be omitted herein, and the main difference between the third embodiment and the second embodiment is as follows: structure of the nebulizer 100 in the present embodiment is provided for implementing the counting function and the initializing function.

Counting Function of Nebulizer According to the Third Embodiment

Figure 22A:
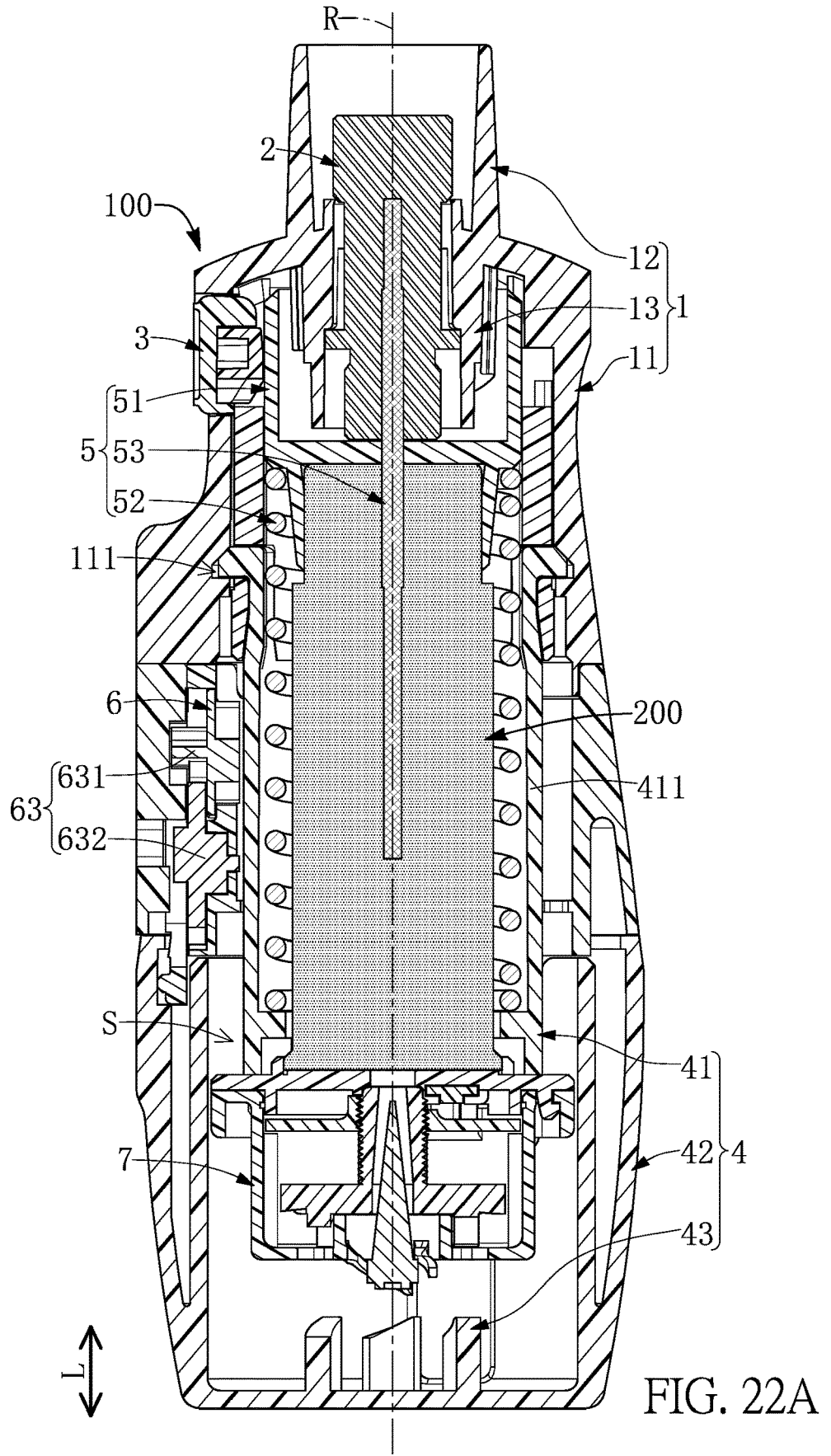
FIG. 22A is a cross-sectional view taken along line XXIIA-XXIIA of FIG. 21.
Figure 22B:
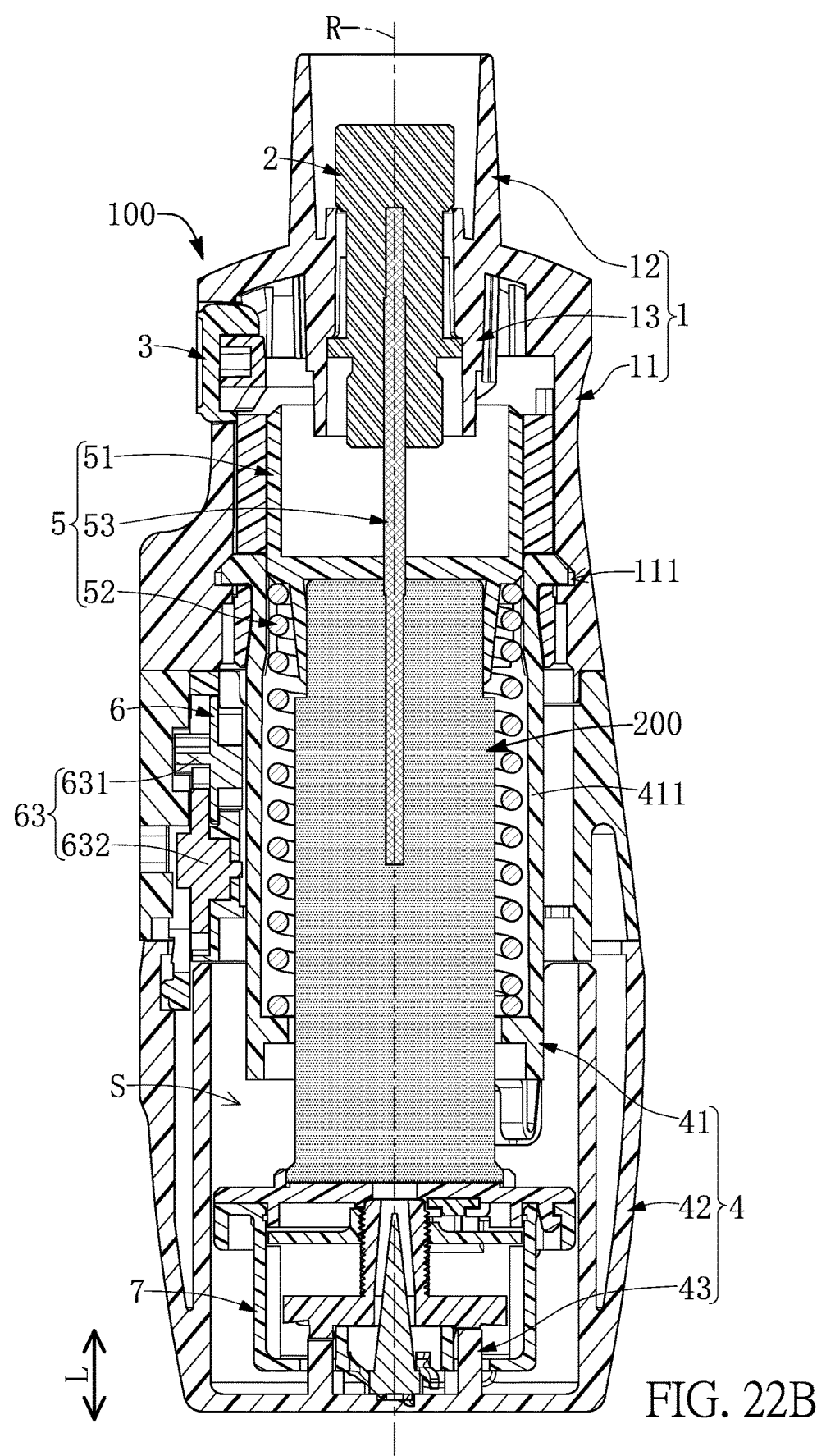
FIG. 22B is a cross-sectional view showing the nebulizer of FIG. 22A at a standby position.
Figure 23:
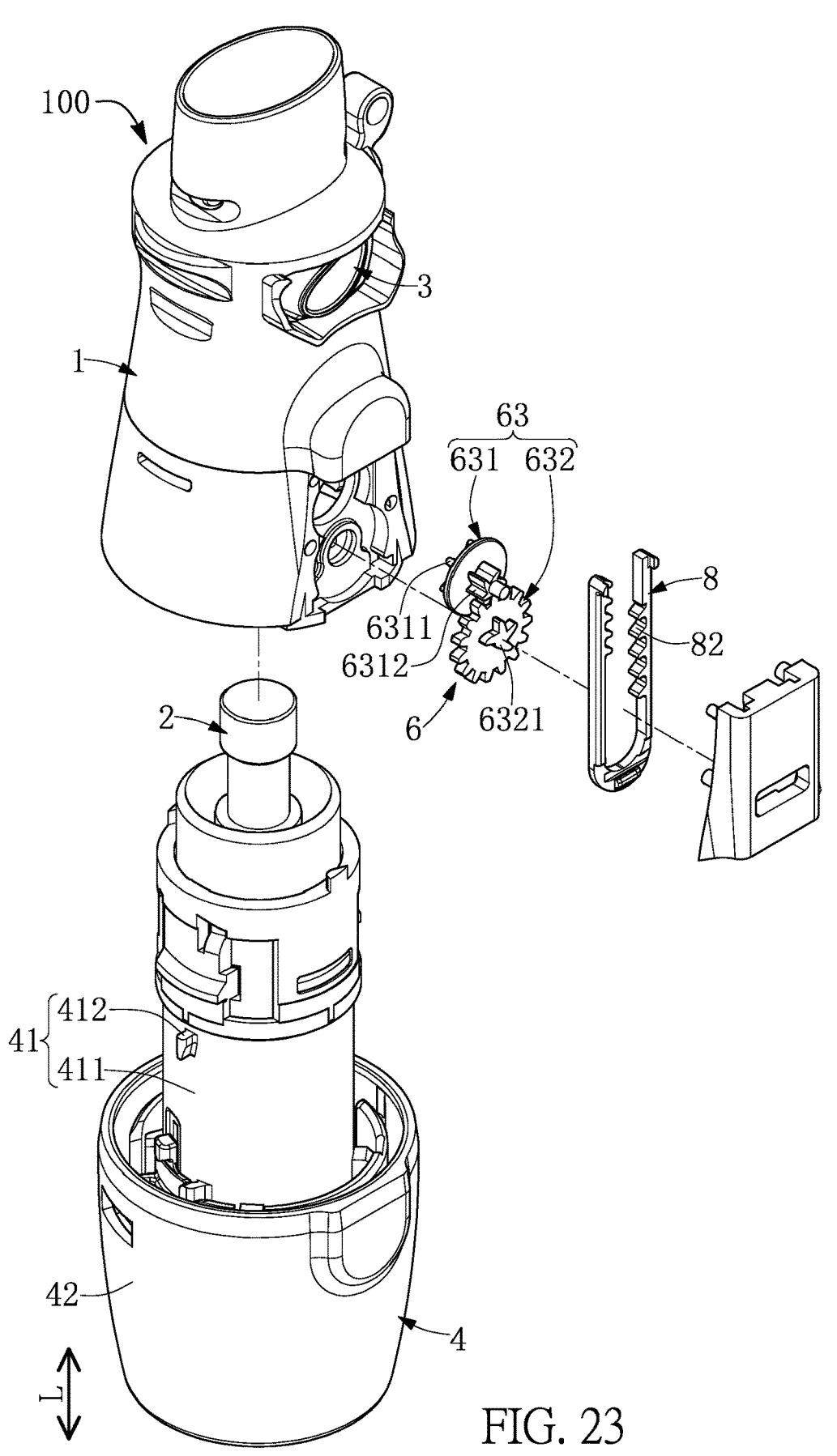
FIG. 23 is an exploded view of the nebulizer of FIG. 21.
Figure 24:
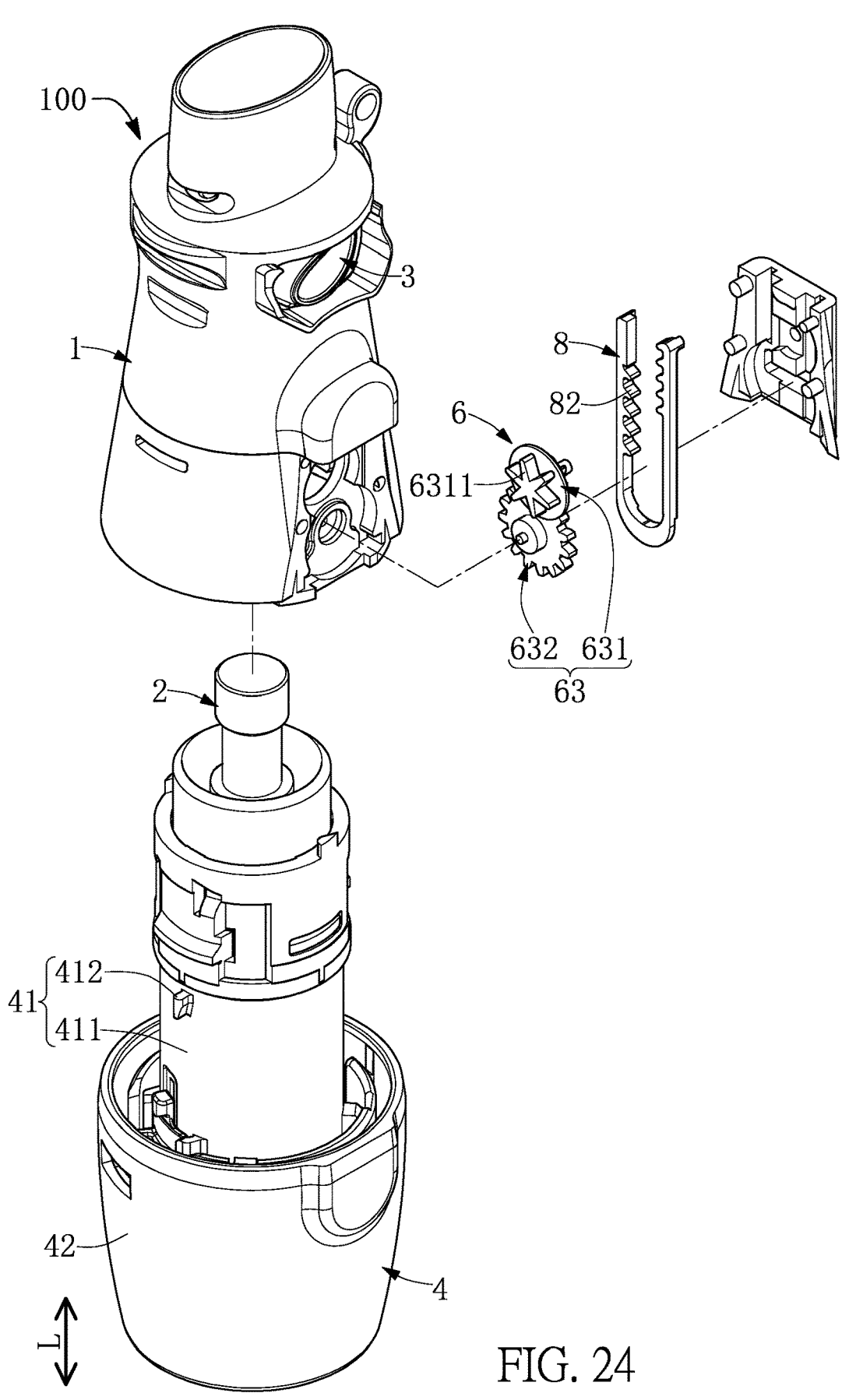
FIG. 24 is an exploded view of the nebulizer of FIG. 21 in another angle of view.

As shown in FIG. 21 to FIG. 23, the rotating mechanism 41 includes a tube 411 and a driving block 412. One end of the tube 411 (e.g., a top end of the tube 411 shown in FIG. 22A) is engaged in the annular slot 111 of the housing segment 11, and another end of the tube 411 is assembled to the cover 42. The driving block 412 is formed on the tube 411 (e.g., the driving block 412 protrudes from an outer surface of the tube 411).

As shown in FIG. 23 to FIG. 25B, (a part of) the counter 6 is located on the movement path of the driving block 412, and the counter 6 includes at least one gear 63 pivotally connected to the casing 1. The at least one gear 63 is located on the movement path of the driving block 412 and includes a plurality of gear teeth 6311. The at least one gear 63 is partially exposed from the housing segment 11 for showing a rotation angle of the at least one gear 63 that can further present how many times of the atomization process have been implemented by the nebulizer 100.

In summary, when the rotating module 4 is rotated by predetermined angle (e.g., when the linking module 5 is moved from the initial position to the standby position), the driving block 412 of the rotating module 41 can push at least one of the gear teeth 6311 so as to drive the counter 6 to be rotated by a counting angle. Specifically, when the rotating module 4 is rotated by the predetermined angle, the driving block 412 pushes at least one of the gear teeth 6311 so as to result a rotation of the counter 6.

Furthermore, a specific structure of the nebulizer 100 for the counting function can be adjusted or changed according to design requirements, so that the following description of the present embodiment only describes one of possible structures of the nebulizer 100, but the present disclosure is not limited thereto.

In the present embodiment, a quantity of the at least one gear 63 is more than one, and the gears 63 are pivotally connected to the casing 1 and are engaged with each other. Specifically, one of the gears 63 has the gear teeth 6311 and is defined as a forward gear 631, and another one of the gears 63 is defined as a counting gear 632 and is partially exposed from the casing 1 for showing a rotation angle of the counting gear 632.

Accordingly, when the rotating module 4 is rotated by the predetermined angle (e.g., when the linking module 5 is moved from the initial position to the standby position), the driving block 412 drives the counting gear 632 to be rotated by the counting angle through the forward gear 631, and a rotation angle of the forward gear 631 is greater than the counting angle.

It should be noted that the counter 6 in the present embodiment is the two gears 63 (e.g., the forward gear 631 and the counting gear 632), but the present disclosure is not limited thereto. For example, in other embodiments of the present disclosure not shown in the drawings, the counter 6 can be provided with at least one transmission gear engaged between the forward gear 631 and the counting gear 632, so that the forward gear 631 can rotate the counting gear 632 through the at least one transmission gear.

Initializing Function of Nebulizer According to the Third Embodiment

The above description describes the counting function of the nebulizer 100 of the present embodiment, and the following description describes the initializing function of the nebulizer 100 of the present embodiment that is in cooperation with the counting function. As shown in FIG. 25A to FIG. 25C, the initializing assembly 8 includes an initializing rack 82. When the rotating module 4 is rotated by the predetermined angle, the driving block 412 of the rotating module 4 drives the counter 6 to be rotated by the counting angle through pushing at least one of the teeth 6311, and the initializing rack 82 is not moved. When the cover 42 is detached from the rotating mechanism 41, the cover 42 drives the initializing rack 82 to be moved, so that the initializing rack 82 reversely rotates the counter 6 to its original position.

Specifically, the at least one gear 63 includes a plurality of initializing teeth 6312 arranged opposite to the gear teeth 6311, and the initializing rack 82 corresponds in position to the initializing teeth 6312. When the cover 42 is detached from the rotating mechanism 41, the cover 42 drives the initializing rack 82 to be moved, so that the initializing rack 82 reversely rotates the at least one gear 63 to its original position by pushing at least one of the initializing teeth 6312.

Moreover, a specific structure of the nebulizer 100 for the initializing function can be adjusted or changed according to design requirements, so that the following description of the present embodiment only describes one of possible structures of the nebulizer 100, but the present disclosure is not limited thereto.

Each of the forward gear 631 and the counting gear 632 has a plurality of initializing teeth 6312, 6321. The initializing teeth 6312 of the forward gear 631 are not engaged with the initializing teeth 6321 of the counting gear 632, and the initializing teeth 6312 and the gear teeth 6311 are respectively arranged on two opposite sides of the forward gear 631. Moreover, the initializing rack 82 has a U-shape and corresponds in position to the initializing teeth 6312 of the forward gear 631 and the initializing teeth 6321 of the counting gear 632.

Accordingly, when the cover 42 is detached from the rotating mechanism 41, the cover 42 drives the initializing rack 82 to be moved, so that the initializing rack 82 reversely rotates the at least one gear 63 to its original position by pushing at least one of the initializing teeth 6312 of the forward gear 631 and at least one of the initializing teeth 6321 of the counting gear 632.

Beneficial Effects of the Embodiments

In conclusion, the counter of the nebulizer provided by the present disclosure is in cooperation with the casing and the rotating module through structural design thereof, so that the counter can show the usage count of the nebulizer through the counting angle, and the user can intuitively obtain a current status of the nebulizer.

Moreover, the locking module of the nebulizer provided by the present disclosure is in cooperation with the casing and the rotating module through structural design thereof, so that after the nebulizer completes the predetermined number of times of the atomization process, the locking module (e.g., the protruding portion) can restrict the rotation of the rotating module for preventing the nebulizer from using the container bottle assembled therein.

Furthermore, the initializing assembly of the nebulizer provided by the present disclosure is in cooperation with the casing and the counter, so that the nebulizer can reset the counting angle of at least one accumulated rotation of the counter to zero through the cover, thereby providing the user with more diverse functions and facilitating the re-use of the nebulizer.

In addition, the nebulizer having the basic configuration can be in cooperation with the counting function and/or the locking function described in any one of the embodiments, and the counting function in any one of the embodiments can be further in cooperation with the corresponding initializing function for effectively providing user with a diverse product.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A nebulizer, characterized by comprising:
a casing defining a rotation axis;
an atomization module fixed in the casing and located at the rotation axis;
a starting module assembled to the casing;
a rotating module including:

a rotating mechanism inserted into the casing and rotatably assembled to the casing along the rotation axis; and
a cover assembled to the rotating mechanism, wherein the cover and the casing jointly define an interior space;
a pusher assembled to an inner bottom of the cover;
a linking module assembled to the rotating module and configured to provide for a container bottle to be disposed therein, wherein the rotating module is rotatable by a predetermined angle to move the linking module, so that the linking module is moved from an initial position to a standby position along the rotation axis by pressing against the casing, and the linking module at the standby position is retained by the starting module;
wherein, when the linking module is at the standby position, the starting module is configured to drive the linking module to be moved to the initial position by being pushed, thereby enabling liquid in the container bottle to be atomized toward an outside of the nebulizer through the atomization module in an atomization process; and
a locking module configured to be connected to a bottom of the container bottle, wherein the locking module includes:
a trigger mechanism corresponding in position to the pusher; and
a locking mechanism assembled to the rotating mechanism, wherein each time the atomization process is completed by the nebulizer, the locking module moves back and forth along the rotation axis once, so that the trigger mechanism is moved toward the locking mechanism through being pressed by the pusher;
wherein, when the nebulizer completes a predetermined number of times of the atomization process, the trigger mechanism pushes the locking mechanism, so that the locking mechanism is moved toward the casing and is then limited in position to restrict a rotation of the rotating mechanism;
wherein the trigger mechanism includes:
a rotation member; and
a progressing member connected to the rotation member, wherein the rotation member is rotatable to drive the progressing member to be moved;
wherein, when the nebulizer completes the predetermined number of times of the atomization process, the progressing member is driven by the rotation member until the locking mechanism is moved by the progressing member, so that the locking mechanism is moved to the casing and limited in position.

2. The nebulizer according to claim 1, wherein the locking module includes a box body configured to be connected to the bottom of the container bottle, wherein the box body has an opening arranged on a movement path of the locking mechanism, and the trigger mechanism is assembled in the box body, and wherein, when the nebulizer completes the predetermined number of times of the atomization process, the progressing member is driven by the rotation member until the opening is closed off by the progressing member and the locking mechanism is pushed by the progressing member.

3. The nebulizer according to claim 2, wherein the casing has a locking slot, and the locking mechanism includes:
an elastic member disposed in the locking slot; and a locking rod having a rod body and a protruding portion that extends from the rod body, wherein the rod body corresponds in position to the opening, and the protruding portion corresponds in position to the locking slot;

wherein, when the nebulizer completes the predetermined number of times of the atomization process, the rod body is moved by the progressing member, so that the protruding portion moves into the locking slot and presses the elastic member.

4. The nebulizer according to claim 1, wherein the locking module includes a box body configured to be connected to the bottom of the container bottle, the trigger mechanism is assembled to the box body and includes a driving member, and the rotation member includes:

a screw rod pivotally connected to the box body, wherein the progressing member is slidably disposed on the box body and is threadedly engaged with the screw rod; and a plurality of teeth disposed on the screw rod, wherein each time the atomization process is completed by the nebulizer, the driving member is configured to be pressed and moved by the pusher in a manner that rotates the screw rod by driving at least one of the teeth to move, such that the progressing member is then driven to be moved.

5. The nebulizer according to claim 4, wherein the driving member includes:

a plate-like body;

a spring abutting against the box body and the plate-like body, wherein the spring tends to push the plate-like body toward a bottom of the box body; and a hook formed on the plate-like body and corresponding in position to at least one of the teeth;

wherein, each time the atomization process is completed by the nebulizer, the plate-like body moves in the box body back and forth once through the pusher and the spring, so that the hook rotates the screw rod by moving at least one of the teeth.

6. The nebulizer according to claim 1, wherein the locking module includes a box body configured to be connected to the bottom of the container bottle, the trigger mechanism is assembled in the box body, and the rotation member includes a turntable corresponding in position to the pusher and a stud that is erectly formed on the turntable, and wherein the progressing member includes:

a progressing plate threadedly engaged with the stud, wherein the turntable is rotatable through being pressed by the pusher so as to drive the progressing plate to be moved along the stud; and a progressing rod slidably disposed on a top of the box body and being separate from the progressing plate;

wherein, when the nebulizer completes the predetermined number of times of the atomization process, the progressing plate is driven by the rotation member until the progressing rod is moved by the progressing plate, so that the progressing rod pushes the locking mechanism to be moved toward the casing and to be limited in position.

7. The nebulizer according to claim 6, wherein the box body has a limiting structure formed on an inner lateral wall thereof and having a first height with respect to a bottom of the box body, wherein the first height is lower than a second height of the stud with respect to the bottom of the box body, wherein, when the progressing plate is located at a position lower than the first height, the progressing plate driven by the turntable is unable to be rotated through being limited by the limiting structure, and is only movable along the stud in a straight line, and wherein, when the progressing plate is located at a position higher than the first height, the progressing plate is configured to be driven by the turntable, so that the progressing plate and the turntable jointly rotate to push the progressing rod.

* * * * *